(12) United States Patent
Antony

(10) Patent No.: US 9,981,000 B2
(45) Date of Patent: May 29, 2018

(54) **COMPOSITION FOR TREATING DIABETES AND DYSLIPIDEMIA OBTAINED FROM THE EXTRACT OF *COSTUS PICTUS* D. DON PLANT AND A METHOD OF PREPARING THE SAME**

(71) Applicant: Merina Benny Antony, Ankamaly (IN)

(72) Inventor: Merina Benny Antony, Ankamaly (IN)

(73) Assignee: ARJUNA NATRUAL EXTRACTS, LTD., Alwaye (IN)

( * ) Notice: Subject to any disclaimer, the term of this patent is extended or adjusted under 35 U.S.C. 154(b) by 277 days.

(21) Appl. No.: 14/577,794

(22) Filed: Dec. 19, 2014

(65) Prior Publication Data

US 2016/0175373 A1      Jun. 23, 2016

Related U.S. Application Data

(63) Continuation of application No. PCT/IN2013/000382, filed on Jun. 20, 2013.

(30) Foreign Application Priority Data

Jun. 22, 2012      (IN) ........................... 2470/CHE/2012

(51) Int. Cl.
    *A61K 36/906*          (2006.01)
    *A61K 36/88*           (2006.01)

(52) U.S. Cl.
    CPC .......... *A61K 36/88* (2013.01); *A61K 2236/00* (2013.01)

(58) Field of Classification Search
    CPC ..................................................... A61K 36/906
    USPC ....................................................... 424/756
    See application file for complete search history.

(56) References Cited

U.S. PATENT DOCUMENTS

| | | |
|---|---|---|
| 6,252,057 B1 | 6/2001 | Brady |
| 6,632,461 B1 | 10/2003 | Slimak |
| 2002/0136777 A1 | 9/2002 | Choi |
| 2002/0172743 A1 | 11/2002 | Chawan |
| 2004/0002423 A1 | 1/2004 | Ohnogi |
| 2005/0031772 A1 | 2/2005 | Gaedcke |
| 2006/0263451 A1* | 11/2006 | Antony ................ A01N 65/00 424/725 |

FOREIGN PATENT DOCUMENTS

| AU | 20023643380 A1 | 10/2003 |
|---|---|---|
| KR | 354912 B | 5/2002 |

OTHER PUBLICATIONS

Thomas et al. "Phytochemical and In-Vitro Anti-Helminthic Studies of Hydor-alcoholic Extract", International Journal of Pharmacy and Pharmaceutical Sciences, vol. 5, Issue 3, 2013.*

Ramachandran, A, Snehalatha, C, Latha, E, Vijay, V, Viswanathan, M, Rising prevalence of NIDDM in an urban population in India, Diabetologia, 40:232-237 (1997).

Rao, RM, Salem, FA, Gleason-Jordan, I, Antidiabetic effects of a dietary supplement "pancreas tonic," J. Natl. Med. Assoc., 90:614-618 (1998).

King, H, Aubert, RE and Herman, WH, Global Burden of Diabetes, 1995-2025, Prevalence, Numerical Estimates, and Projections, Diabetes Care, 21(9):1414-1431 (1998).

Zhou, J, Wang, X, Pineyro, MA and Egan, JM, Glucagon-like Peptide I and Exendin-4 Convert Pancreatic AR42J Cells Into Glucagon- and Insulin-Producing Cells, Diabetes, 48:2358-2366 (Dec. 1999).

Xu, G, Stoffers, DA, Habener, JF and Bonner-Weir, S, Exendin-4 Stimulates Both β-Cell Replication and Neogenesis, Resulting in Increased β-Cell Mass and Improved Glucose Tolerance in Diabetic Rats, Diabetes, 48:2270-2276 (Dec. 1999).

American Diabetes Association, Type 2 Diabetes in Children and Adolescents, Diabetes Care, 23(3):381-389 (Mar. 2000).

Zimmet, P, Alberti, KGMM and Shaw, J, Global and Societal Implications of the Diabetes Epidemic, Nature, 414:782-787 (Dec. 13, 2001), Macmillan Magazines Ltd.

Nahar, N, Mosihuzzaman, M, and Khan, SH, Determination of Free Sugars in Plant Materials having Antidiabetic Activity, Dhaka Univ. J. Sci., 46(1):167-170 (Jan. 1998).

Mosihuzzaman, M, Nahar, N, Ali, L, Rokeya, B, Azad Khan, AK, Nur-E-Alam, M and Nandi,RP, Hypoglycemic Effects of Three Plants from Eastern Himalayan Belt, Diabetes Research, 26(33):127-138 (1994), Teviot-Klimpton Publications.

Basualdo, I, Zardini, E, and Ortiz, M, Medicinal Plants of Paraguay: Underground Organs, Economic Botany, 45(1):86-96 (1991), New York Botanical Garden, Bronx, NY 10458.

Anaga, AO, Njoku, CJ, Ekejiuba, ES, Esiaka, MN, and Asuzu, IU, Investigations of the Methanolic Leaf Extract of *Costus afer*. Ker for Pharmacological Activities in vitro and in vivo, Phytomedicine, 11:242-248 (2004), Elsevier.

Griffin, BW, Chandler, ML, and DeSantis,L,Prevention of Diabetic Cataract and Neuropathy in Rats by Two New Aldose Reductase Inhibitors, Invest Ophthal. Vis. Sci. vol. 25 (Supplement), p. 136, ARVO Abstract No. 36 (Mar. 1984).

(Continued)

*Primary Examiner* — Christopher R Tate
*Assistant Examiner* — Deborah A Davis
(74) *Attorney, Agent, or Firm* — Jyoti C. Iyer

(57) ABSTRACT

The disclosure provides a medicinal composition for treating diabetes and dyslipidemia obtained from the extract of *Costus pictus* D. Don. The extract of *Costus pictus* D. Don includes hydroxycinnamic acid derivatives and flavonol mono-, di- and triglycosides along with small amounts of free flavonols. The extract of *Costus pictus* D. Don has low levels of oxalic acid and/or oxalates. The hydroxycinnamic acid derivatives include caffeic acid, p-coumaric acid, ferulic acid and sinapic acid and flavonol mono-, di- and triglycosides which include quercetin, kaempferol and isorhamnetin with sugars glucose, galactose and rhamnose. Disclosure also provides a method of preparing the extract of *Costus pictus* D. Don of the same. The disclosure also provides a method of treating mammals including human beings for medical conditions such as diabetes; dyslipidemia and related conditions; for increasing anti oxidant potential; for the regeneration of pancreatic beta cells and increasing the insulin secretogogue effect.

8 Claims, 17 Drawing Sheets

(56) References Cited

OTHER PUBLICATIONS

Katzung, BG, (editor), Basic and Clinical Pharmacology, International Edition (8$^{th}$ Edition), pp. 723-730 (2001), Appleton & Lange.

Harris, MI, Flegal, KM, Cowie, CC, Eberhardt, MS, Goldstein, DE, Little, RR, Wiedmeyer, MS, Bryd-Holt, DD, Prevalence of Diabetes, Impaired Fasting Glucose, and Impaired Glucose Tolerance in U.S. Adults, Diabetes Care, 21(4):518-524 (Apr. 1998).

One (1) page of International Search Report dated Aug. 11, 2005, for PCT/IN04/00019.

Khan, MMAA, Singh, N, Dhawan,KNI, Occurrence and identification of a new antiviral saponin from Lawsonia alba Lam. Fruits, Nat.Acad.Sci.Letters 19(7&8): 145-148, 1996.

Sarin, YK, Bedi, KL, Atal, CK, Costus speciosus rhizome as source of diosgenin, Indian Academy of science, 1974; 43(18):569-70.

Jung, MJ, Chung, HY, Choi, JS, Antioxidant activity of roasted defatted perilla seed, Natural Product sciences, 7(3): 72-75, 2001.

Sathishraj, R , Augustin,A, Oxalic acid and oxalate oxidase enzyme in Costus pictus D. Don, Acta Physiol Plant, DOI 10.1007/s11738-011-0866-x.

Brodoff, BN, Penhos, JC, Levine, R, The Effect of Feeding and Various Hormones on the Glucose Tolerance of the Sand Rat (*Psammomys obesus*), Diabetologia 3, 167-170(1967).

Kobayashi, Y, Ohashi, S, and Takeuchi, S, Effect of the Salts of Meso-Oxalic acid on Alloxan Diabetes Mellitus, Jap.J. Pharmacol. 1, 9 (1951).

Jayasri, MA, Gunasekaran, S, Radha,A,Mathew, TL, Anti-diabetic effect of *Costus pictus* leaves in normal and streptozotocin-induced diabetic rats, Int J Diabetes & Metabolism 16: 117-122(2008).

Jothivel, N, Ponnusamy, SP, Appachi, M, Singaravel, S, Rasilingam, D, Deivasigamani,K, Thangavel,S, Anti-diabetic Activity of Methanol Leaf Extract of *Costus pictus D. Don* in Alloxan induced Diabetic rats, Journal of Health Science,53(6),655-663(2007).

Gao, Hy,Yaylayan,VA, Yeboah, F, Oxalic Acid-Induced Modifications of Postglycation Activity of Lysozyme and its Glycoforms, J. Agric. Food Chem , 58, 6219-6225 (2010).

The European Agency for the evaluation of medicinal products veterinary medicines and inspections, Committee for veterinary medicinal products Dec. 2003.

Schneider, A, The Probable Function of Calcium Oxalate Crystals in Plants, Botanical Gazette, vol. 32, No. 2 (Aug. 1901), pp. 142-144.

\* cited by examiner

COMPOSITION FOR TREATING DIABETES AND DYSLIPIDEMIA OBTAINED FROM THE EXTRACT OF *COSTUS PICTUS D. DON* PLANT AND A METHOD OF PREPARING THE SAME

This application is a continuation of International Application Serial No. PCT/IN2013/000382, filed Jun. 20, 2013, which claims priority of Indian Provisional Application Serial No. 2470/CHE/2012, filed Jun. 22, 2012, all of which applications are hereby incorporated by reference.

FIELD OF INVENTION

The disclosure relates to an extract of *Costus pictus* D. Don having low oxalic acid and/or oxalates content and method of producing the said extract and more specifically a composition for treating diabetes and dyslipidemia obtained from the extract of *Costus pitcus* D. Don plant and a method of producing the same. The constituents of the said extract of *Costus pictus* D. Don having low oxalic acid and/or oxalates content containing hydroxycinnamic acid derivatives which include caffeic acid, p-coumaric acid, ferulic acid and sinapic acid and flavonol mono-, di- and triglycosides wherein said Flavonol mono-, di- and triglycosides include quercetin, kaempferol and isorhamnetin with sugars glucose, galactose & rhamnose along with small amounts of free flavonols which is used for treating diabetes, dyslipidemia and related disorders. These lipids include cholesterol, cholesterol esters, phospholipids, and triglycerides. Lipids are transported in the blood as large 'lipoproteins'.

BACKGROUND

Diabetes mellitus was known to ancient Indians as early as sixth century B. C. Charaka in his "Charaka Samhita" has mentioned the sweetness of urine in addition to polyuria. The Indian physician Susruta in 500 A.D described the disease as "Madhumeha" meaning rain of honey, (due to the phenomenon of attracting ants near the urine of a diabetic patient) with symptoms of foul breath, voracious appetite and languor. Other early Indian writings like Astangahrayda, Bhava-prakasa, Madhav-nidana etc. have also described diabetes. Globally, the number of people with diabetes is expected to rise from the current estimate of 150 millions to 220 millions in 2010 and 300 millions in 2025. The prevalence is increasing in the developing countries such as India, particularly in urban areas. The estimated number of diabetes patients in India was 19.4 million in 1995 and are expected to be 57.2 million in 2025 (W.H.O). In the United States, it is estimated that as of 2011, 25.8 million people (8.3% of the total population) were diabetic. About 2.15 lakhs of people under 20 years of age have diabetes (0.26% of all people in this age group). Approximately one in every 400-500 children and adolescents has Type-1 diabetes. In the age group of 20 years or older, 25.6 million (11.8% in men and 10.8% in women) have diabetes. In people above the age of 60 years, 10.9 million (26.9% of all people in this age group) have diabetes.

There are mainly two types of diabetes. Type-1 diabetes which was previously called insulin dependent diabetes mellitus (IDDM) or juvenile-onset diabetes. This develops when the body's immune system destroys pancreatic beta cells ($\beta$-cells), which are the only cells in the body that make the hormone insulin that regulates blood glucose level. Type-II diabetes was previously called non-insulin dependent diabetes mellitus (NIDDM) or adult onset diabetes. It usually begins as insulin resistance, a disorder in which the cells of the body fails to respond to insulin properly.

Unlike what was happening a few decades ago, antidiabetic herbal formulations are marketed now in plenty in the form of powders, tablets, capsule and liquid preparations. Most of these have not undergone controlled clinical trials. Usually herbs with reputed anti-diabetic activity as documented in standard ayurvedic books or knowledge gained from experienced Ayurvedic practitioners are taken up and mixtures are prepared with arbitrary dosage. It is doubtful how some of these preparations are effective and what are the side effects, on long term usage are.

The medicinal plant *Costus pictus* D. Don is a very popular and fast-spreading ginger belonging to the family of Zingiberaceae that has been used as an ornamental climbing plant and is used as a munching dietary supplement for the treatment of diabetes in southern India. *Costus pictus* D. Don, commonly called as Spiral ginger, Stepladder or Insulin plant, belongs to the family Costaceae. The plant is cultivated as an ornamental plant in tropical gardens. It is a perennial herb growing up to 2-3 m and spreads 1.5-2 m. The glossy linear narrow leaves with characteristic wavy edges are arranged spirally on red coloured stem. The leaves are less fleshy and have an acrid taste. The inflorescences form both at the end of a leafy stem, and less often radically on a short nearly leafless stem. It can be recognized by its yellow flowers with red spots and stripes and appear in terminal cone. Propagation is carried out through stem cuttings and rhizome.

Different extracts of *Costus pictus* D. Don obtained from various parts of *Costus pictus* D. Don is reported to have different properties.

*Costus pictus* D. Don extracts have high concentration of oxalic acid. Since oxalic acid is found in high concentration in *Costus pictus* D. Don and found to be toxic, we standardized a method of making *Costus pictus* D. Don extract with very low level of oxalic acid content.

Oxalic acid is an organic compound with the formula $H_2C_2O_4$. It is a colorless crystalline solid that dissolves in water to give colorless solutions. It is classified as a dicarboxylic acid.

Oxalic acid is reported to be toxic for oral administration (Merck Index, thirteenth edition, page 1237, para 6980: The European Agency for the evaluation of medicinal products veterinary medicines and inspections, Committee for veterinary medicinal products December 2003: Side effects of oxalic acid, Tracey Roizman D C, 2011).

*Costus pictus* D. Don extract (alcoholic, aqueous and juice extracts of leaves/whole plant) is reported to have anti diabetic property (U.S. Pat. No. 7,255,886, Merina Benny (2007); Nandhakumar Jothivel et al (2007): M A Jayasri et al (2008)).

*Costus pictus* D. Don is reported to contain oxalic acid (Camargo et al 0.2006; Moron et al. 2007). The leaves of *Costus pictus* D. Don are sour in taste due to the presence of high levels of oxalic acid in the leaves. (Rajendran Sathishraj et al, 2011).

*Costus pictus* D. Don extracts have high concentration of oxalic acid. If it is in small quantity it may not be that harmful and on the contrary may be beneficial against diabetes (Oxalic acid—Induced Modification of Postglycation Activity of Lysozyme and its Glycoforms (Hong Ying Gao et al, 2010). But Oxalic acid is known to produce Kidney stones. (Effect of dietary oxalate and calcium on urinary oxalate and risk of formation of calcium oxalate kidney stones, Linda K Massey, 1993).

In view of the above, we have developed a method of preparing an extract of Costus pictus D. Don having low oxalic acid and/or oxalates content and composition of Costus pictus D. Don extract having low oxalic acid and/or oxalates content. The disclosure not only provides a method of preparation of an extract of Costus pictus D. Don having low oxalic acid and/or oxalates content, but also a composition derived from therein. The constituents of the said extract of Costus pictus D. Don having low oxalic acid and/or oxalates content contain hydroxycinnamic acid derivatives and flavonol mono-, di- and triglycosides along with small amounts of free flavonols which is used for treating diabetes, dyslipidemia and related disorders.

SUMMARY

Disclosure provides an extract of Costus pictus D. Don. Constituents of the extract include hydroxycinnamic acid derivatives and flavonols. In some embodiments of the extracts, the total content of the oxalic acid and oxalates is less than about 15%. The disclosure provides an extract of Costus pictus D. Don having low oxalic acid/oxalate content as well as a medical composition useful for treatment of diabetes; treatment of dyslipidemia and related conditions; for increasing anti oxidant potential; for the regeneration of pancreatic beta cells and increasing the insulin secretogogue effect for mammals including human beings.

Further the disclosure also provides a method of preparation of an extract of Costus pictus D. Don having low oxalic acidioxalates content having the said medicinal composition.

Disclosure also discloses a method of treating mammals including human beings for medical conditions selected from diabetes; dyslipidemia and related conditions; for increasing antioxidant potential; for the regeneration of pancreatic beta cells and increasing the insulin secretogogue effect.

In some embodiments, the constituents of hydroxycinnamic acid derivatives include caffeic acid at a concentration of about 0.1% and above, p-coumaric acid at a concentration of about 0.1% and above, ferulic acid at a concentration of about 0.1% and above and sinapic acid at a concentration of about 0.1% and above. Some embodiments, of the extract also contain components as acid derivatives, glucosides or in free form. Some embodiments include flavonol mono-, di- and triglycosides which include quercetin at a concentration of about 0.1% and above, kaempferol at a concentration of about 0.1% and above and isorhamnetin at a concentration of about 0.1% and above with sugars glucose, galactose and rhamnose. In addition it also contains small amounts of free flavonols comprises quercetin at a concentration of about 0.1% and above, kaempferol at a concentration of about 0.1% and above and isorhamnetin at a concentration of about 0.1% and above.

The extract of Costus pictus D. Don can be derived from fresh whole plant, fresh leaves, dried leaves or dried leaf powder, juice of fresh leaves, fresh or dried aerial parts of Costus pictus D. Don or combinations thereof.

The method of producing the said composition includes the steps of; a) selecting the raw material and cleaning to make it free of any foreign matter like dirt b) cutting the cleaned material into small pieces c) extraction with solvents selected from water, hexane, methanol, ethanol, isopropanol, n-butanol, methyl acetate, ethyl acetate, propyl acetate, n-butyl acetate and combinations thereof to obtain an extract d) removal of oxalic acid from the extract by heating the extract with water at 80° C. e) purifying and concentrating the resultant extract and dry to obtain in dry powder form.

Another embodiment provides extract of Costus pictus D. Don prepared from fresh leaves of Costus pictus D. Don by extraction with 90% methanol and oxalic acid content in the extract is reduced by heating the extract with water at 80° C.

Yet another embodiment provides a methanol extract of Costus pictus D. Don having low oxalic acid and/or oxalates content is purified by passing through a silica column.

In another embodiment methanol extract of Costus pictus D. Don having low oxalic acid and/or oxalates content is again extracted with ethyl acetate.

In general said composition, the extract of Costus pictus D. Don will be having an oxalic acid and/or oxalates content as follows:
  a) about 10% and below, if it is a methanol extract;
  b) about 5% and below, if said methanol extract is further purified;
  c) about 2.5% and below, if it is an ethyl acetate extract;
  d) about 1% and below, if it is a purified ethyl acetate extract.

BRIEF DESCRIPTION OF THE DRAWINGS

Other features and advantages of the disclosure should become apparent from the following description and read in conjunction with the figures of the accompanying drawings, which demonstrate the findings of various process trials carried under certain embodiments under the disclosure as well as the findings.

Don (sample 2 prepared as per example 1), the extract had low oxalic acid and/or oxalates content.

Figure 6B:
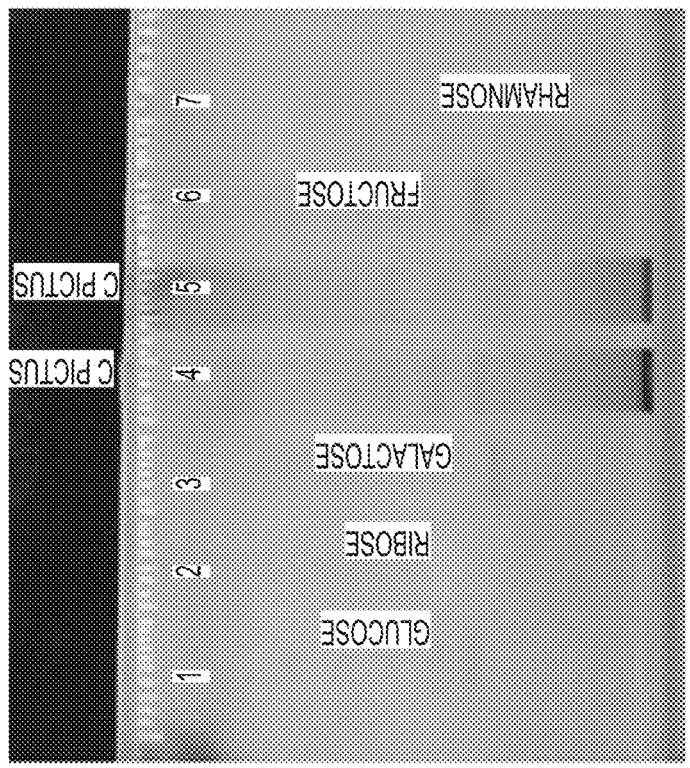
Figure 6A:
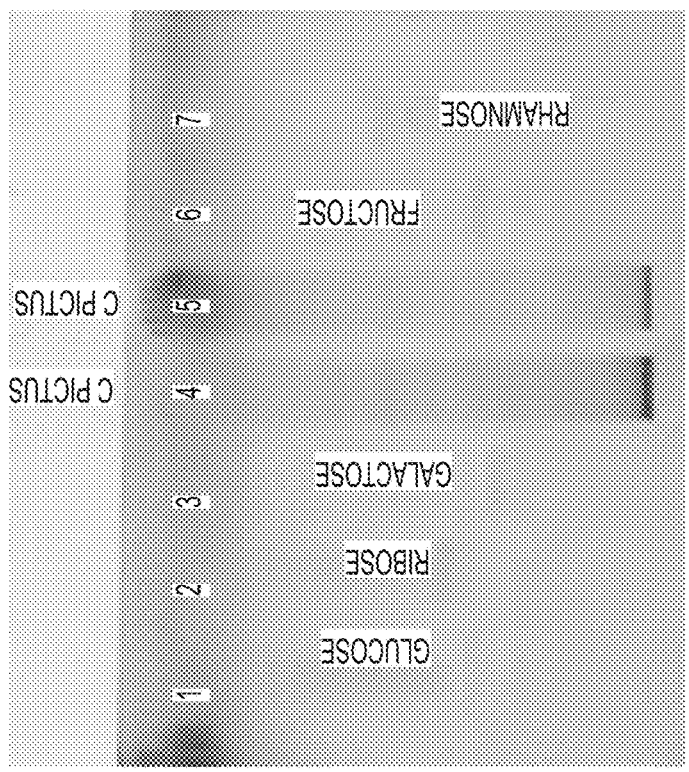

FIG. 6a. shows the presence of sugars (glucose, galactose and rhamnose) by High performance thin layer chromatography (HPTLC) at visible light of acid hydrolysed 90% methanol extract of fresh leaves of Costus pictus D. Don, the extract had low oxalic acid and/or oxalates content (sample 2 prepared as per example 1).

FIG. 6b shows the presence of sugars (glucose, galactose and rhamnose) on High performance thin layer chromatography (HPTLC) at UV light of acid hydrolysed 90% methanol extract of fresh leaves of Costus pictus D. Don, the extract had low oxalic acid and/or oxalates content (sample 2 prepared as per example 1).

Figure 7:
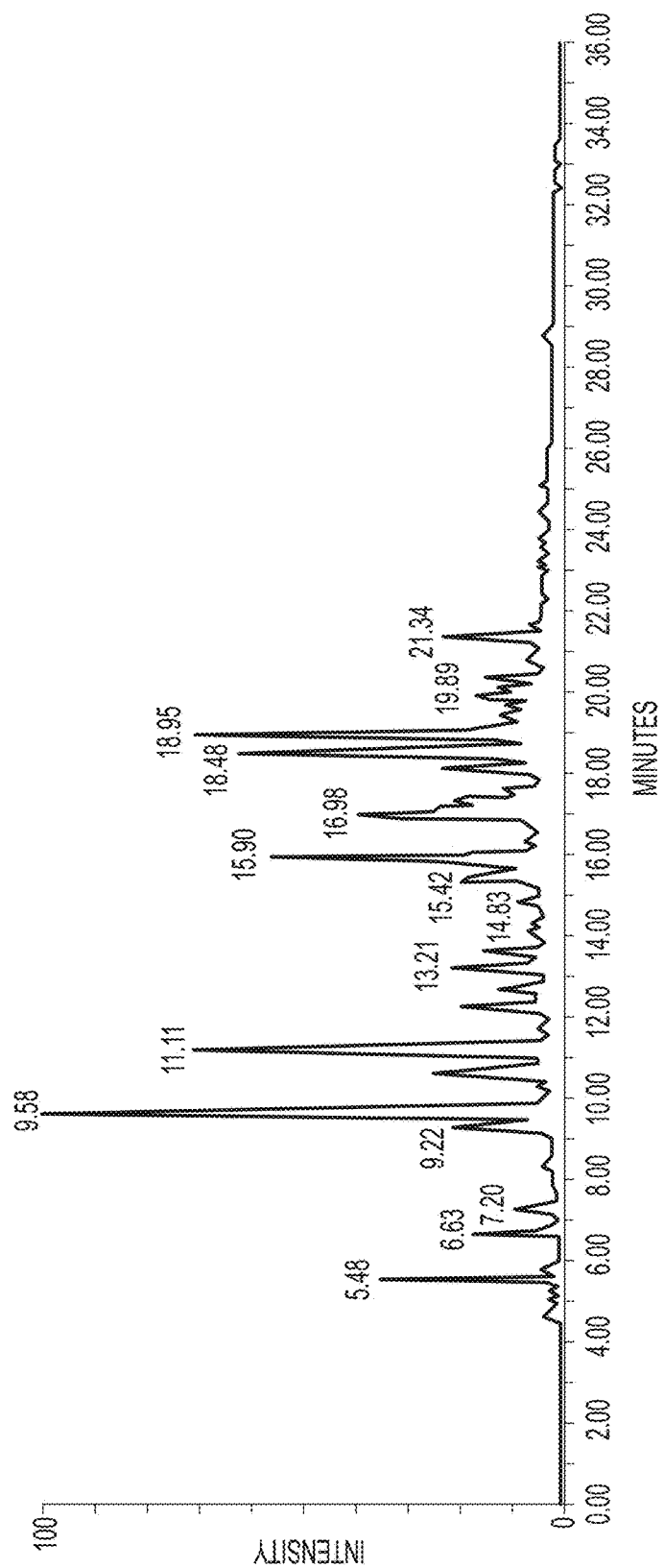

FIG. 7 provides Photodiode array detector (PDA) plots at 324 nm from the LCMS (Liquid chromatography-mass spectrometry) run of 90% methanol extract of fresh leaves of Costus pictus D. Don, the extract had low oxalic acid and/or oxalates content (sample 2 prepared as per example 1).

Figure 8:
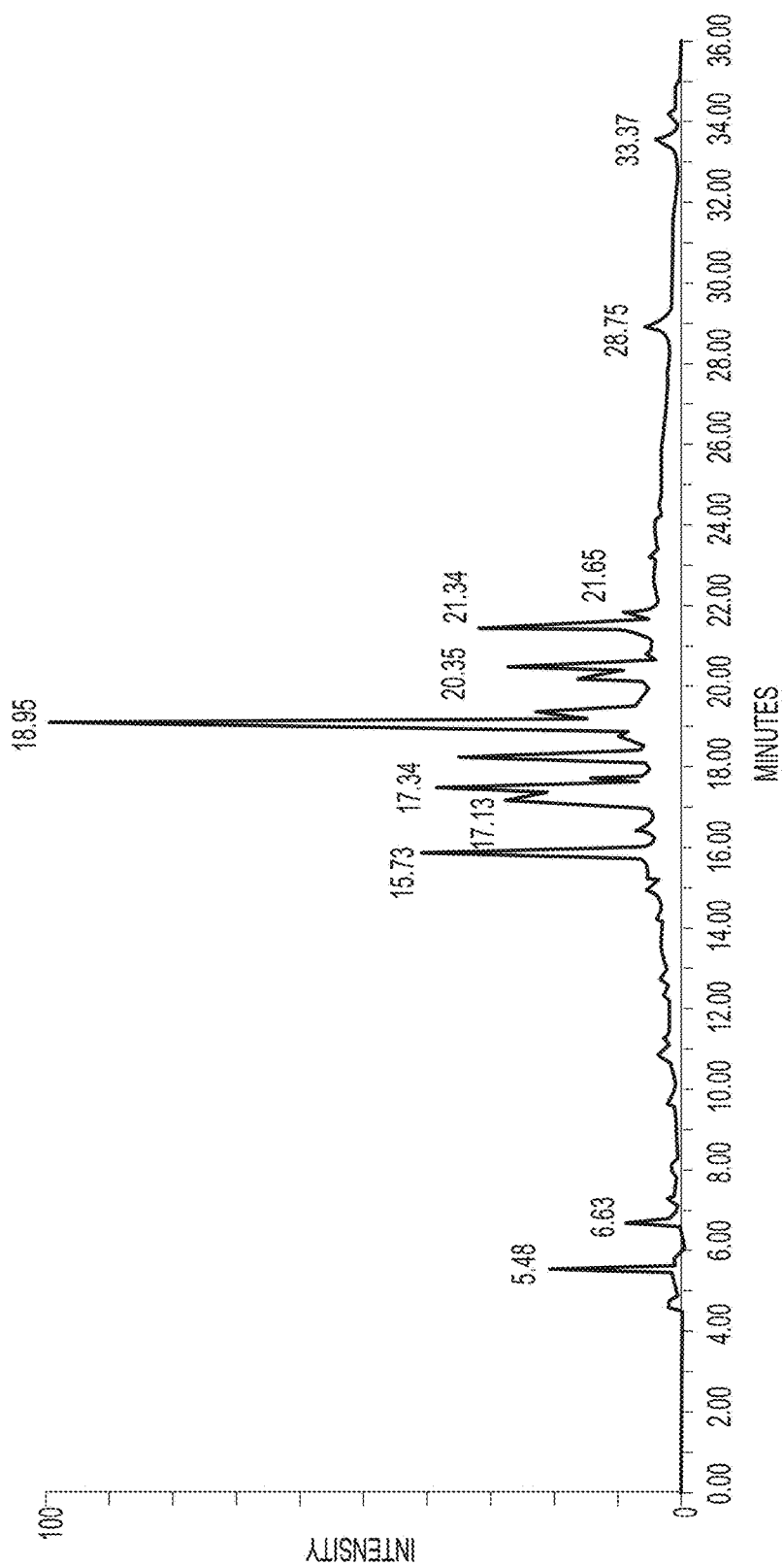

FIG. 8 provides Photodiode array detector (PDA) plots at 370 nm from the LCMS (Liquid chromatography-mass spectrometry) run of 90% methanol extract of fresh leaves of Costus pictus D. Don, the extract had low oxalic acid and/or oxalates content (sample 2 prepared as per example 1).

Figure 9:
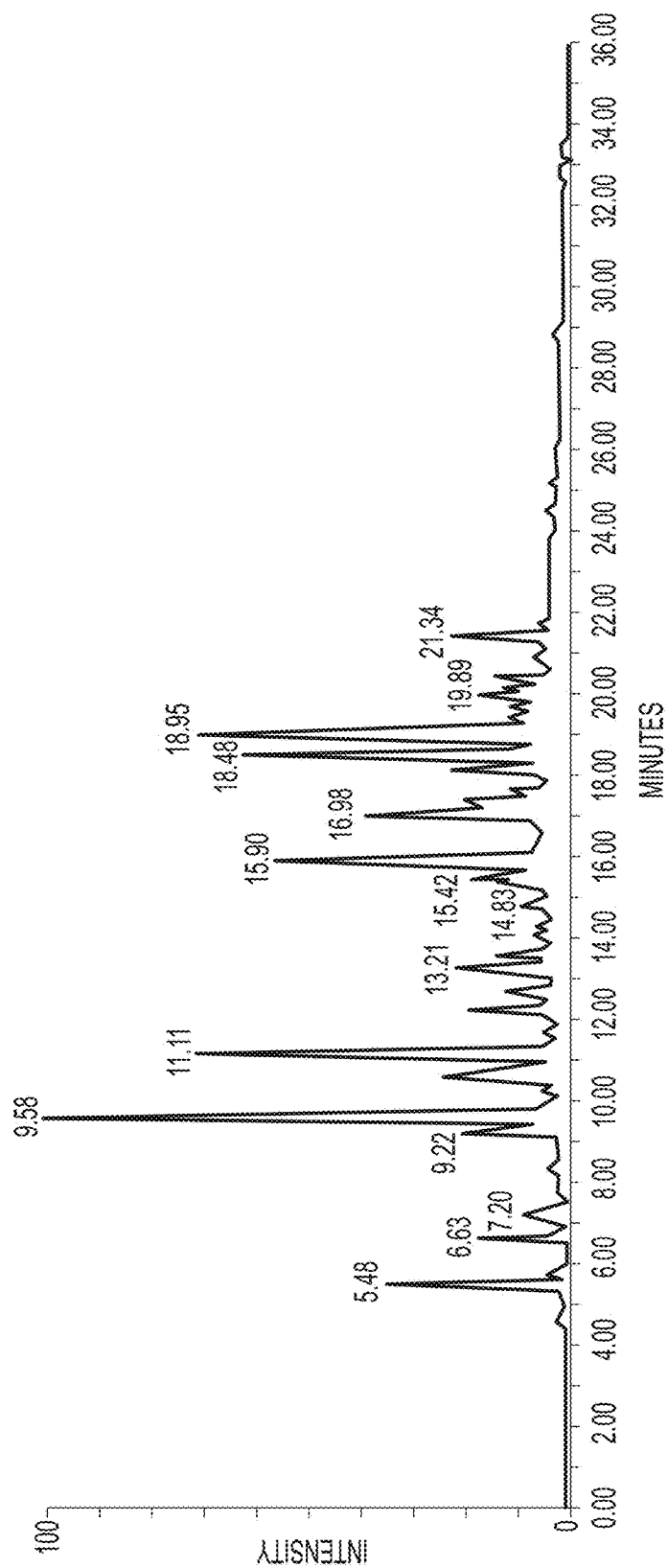

FIG. 9. shows primarily hydroxycinnamic acid derivatives on a photodiode array detector (PDA) plot at 324 nm from LCMS (Liquid chromatography-mass spectrometry) run of 90% methanol extract of fresh leaves of Costus pictus D. Don, and the extract had low oxalic acid and/or oxalates content (sample 2 prepared as per example 1).

Figure 10:
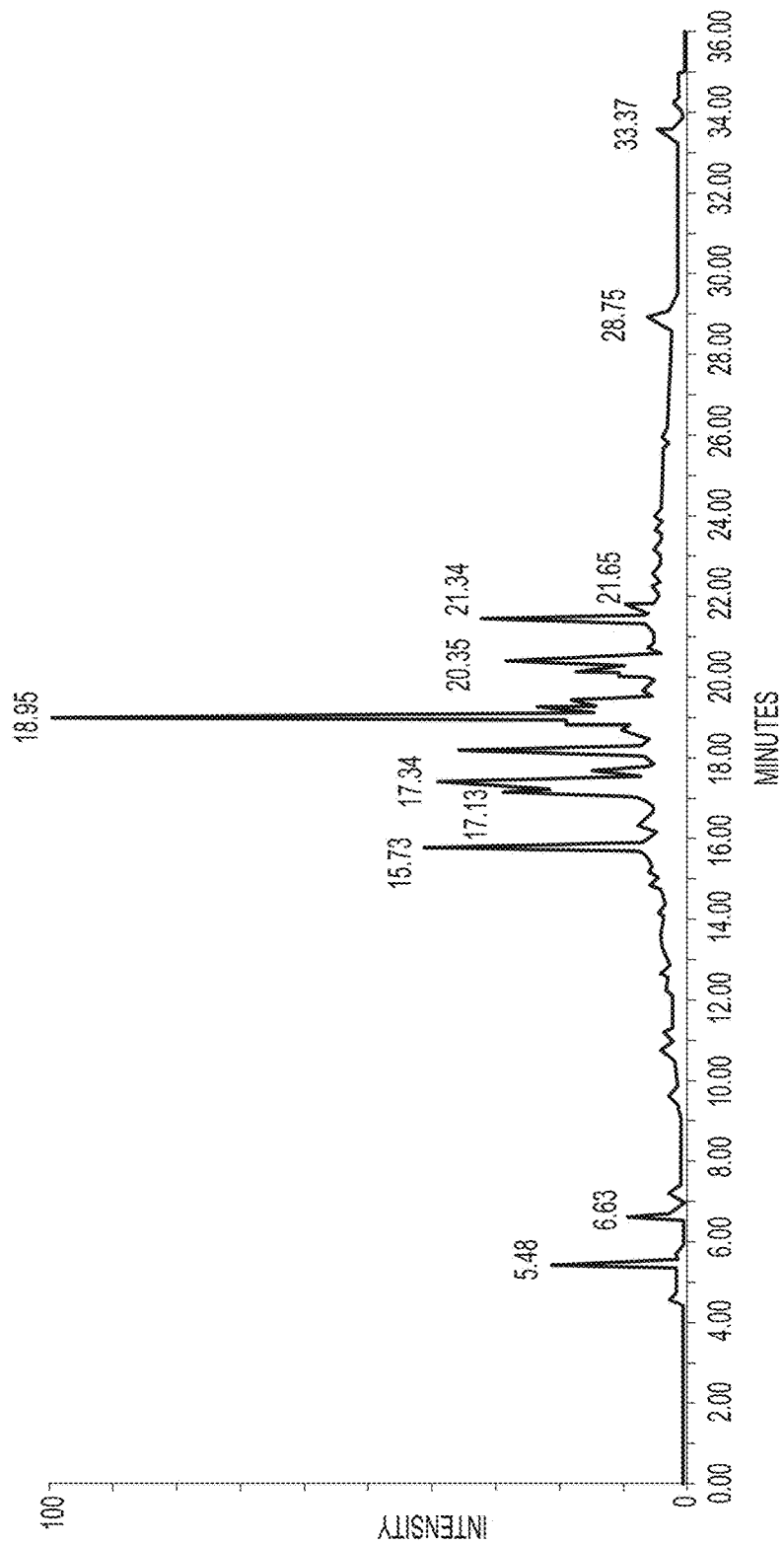

FIG. 10. shows presence of flavonoid derivatives on Photodiode array detector (PDA) plot at 370 nm from LCMS (Liquid chromatography-mass spectrometry) run of 90% methanol extract of fresh leaves of Costus pictus D. Don, the extract had low oxalic acid and/or oxalates content (sample 2 prepared as per example 1).

Figure 11:
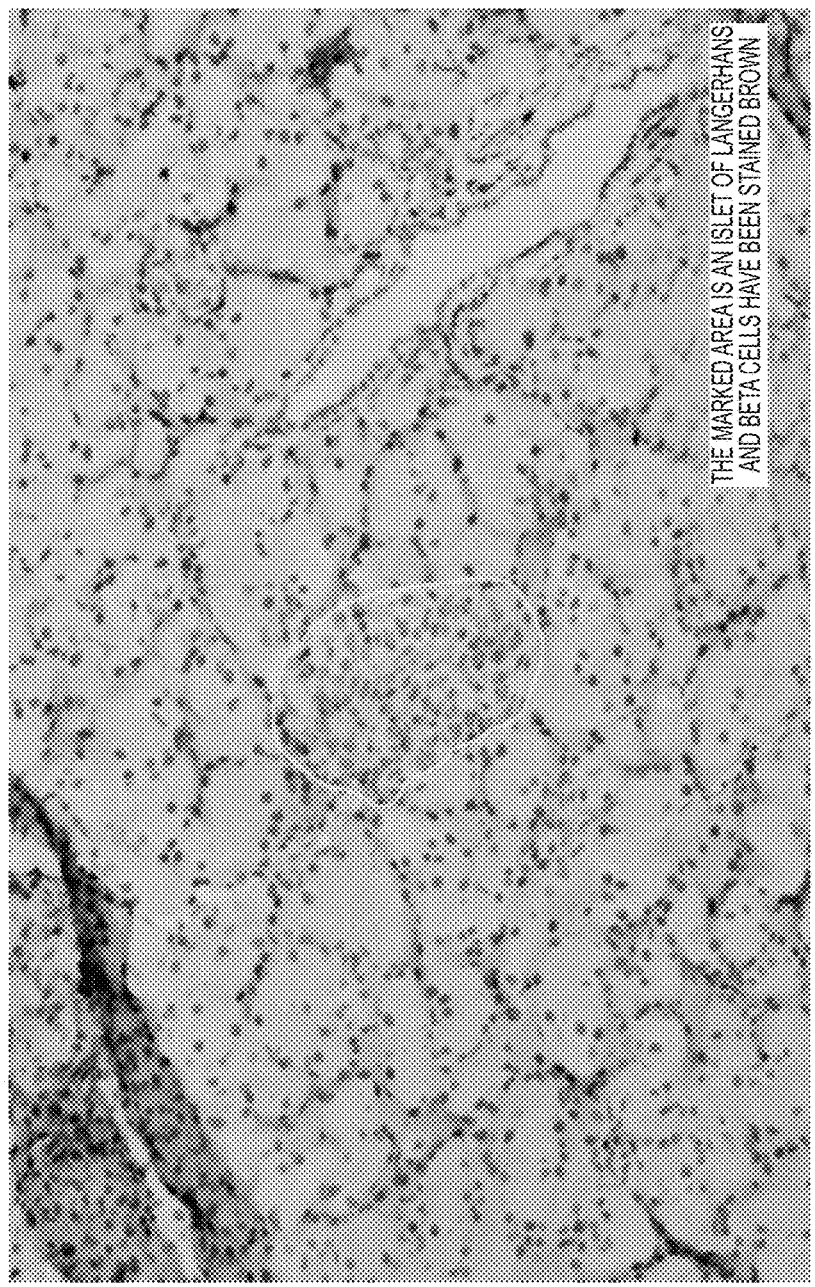

FIG. 11. Histopathological examination of the pancreas of normal group. The marked area depicts an islet of Langerhans with the beta cells stained brown.

Figure 12:
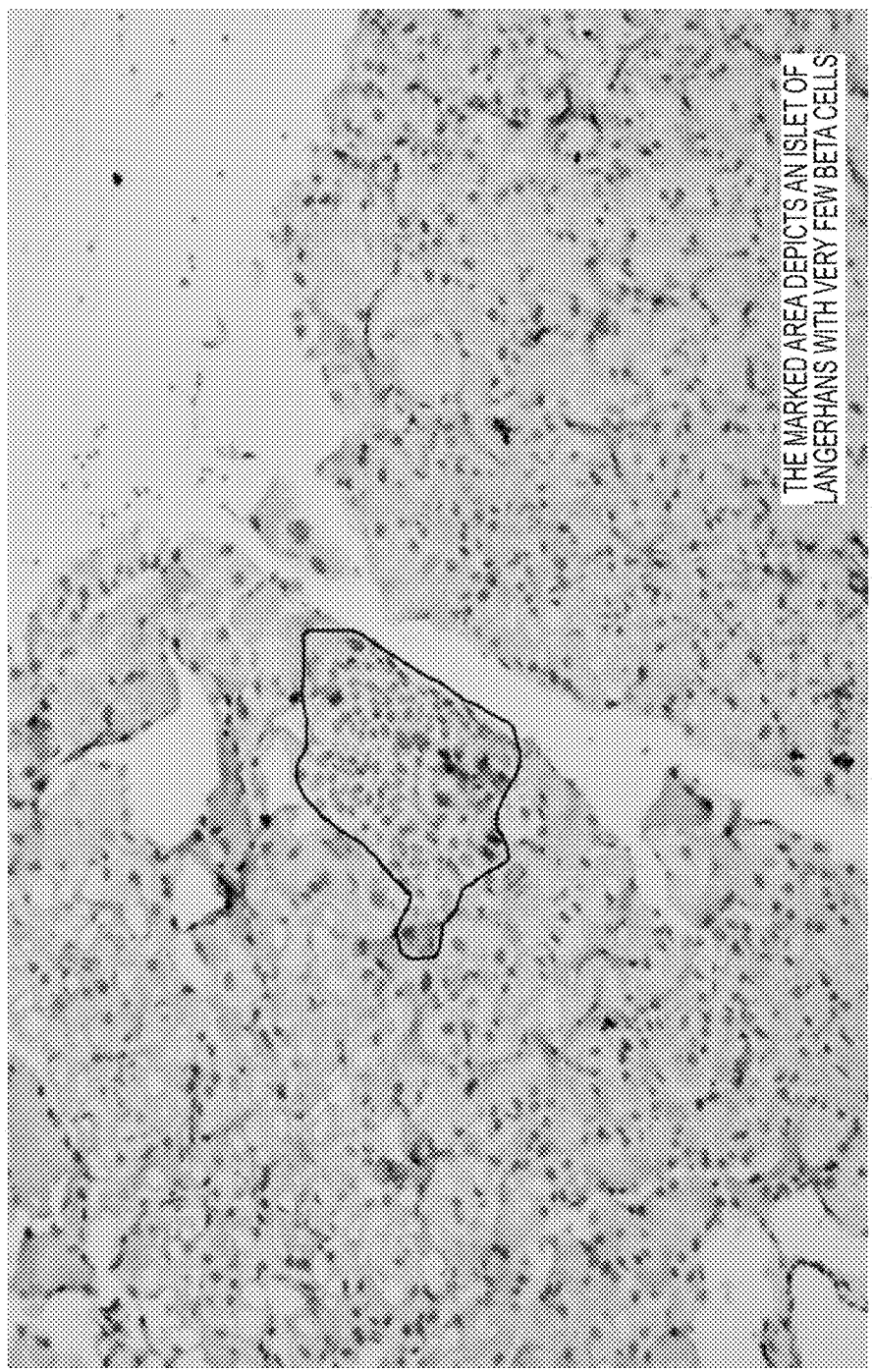

FIG. 12. Histopathological examination of the pancreas of Diabetic control group. The marked area depicts an islet of Langerhans with very few beta cells.

Figure 13:
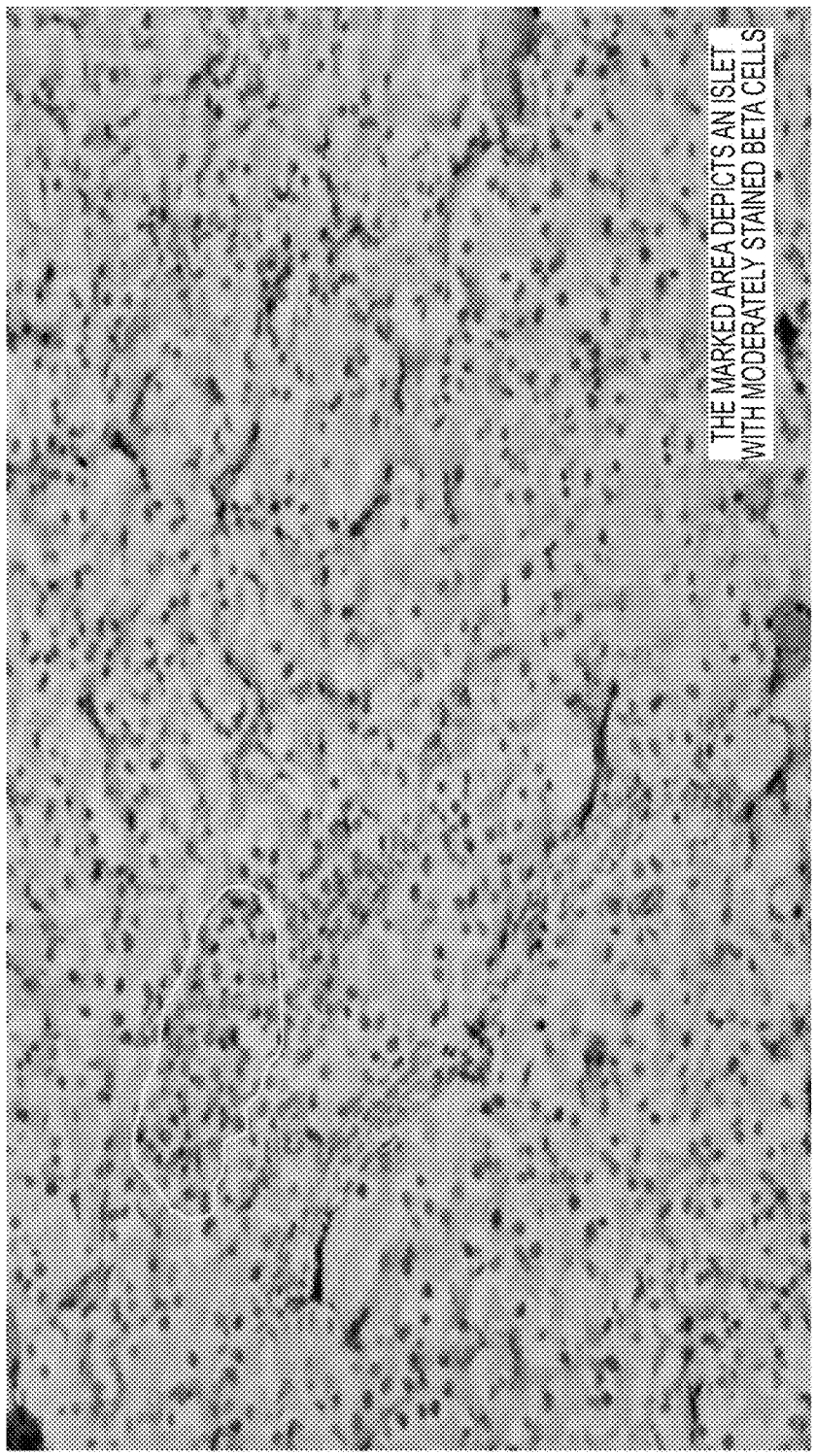

FIG. 13. Histopathological examination of the pancreas of Glibenclamide treated group. The marked area depicts an islet of Langerhans with moderately stained beta cells.

Figure 14:
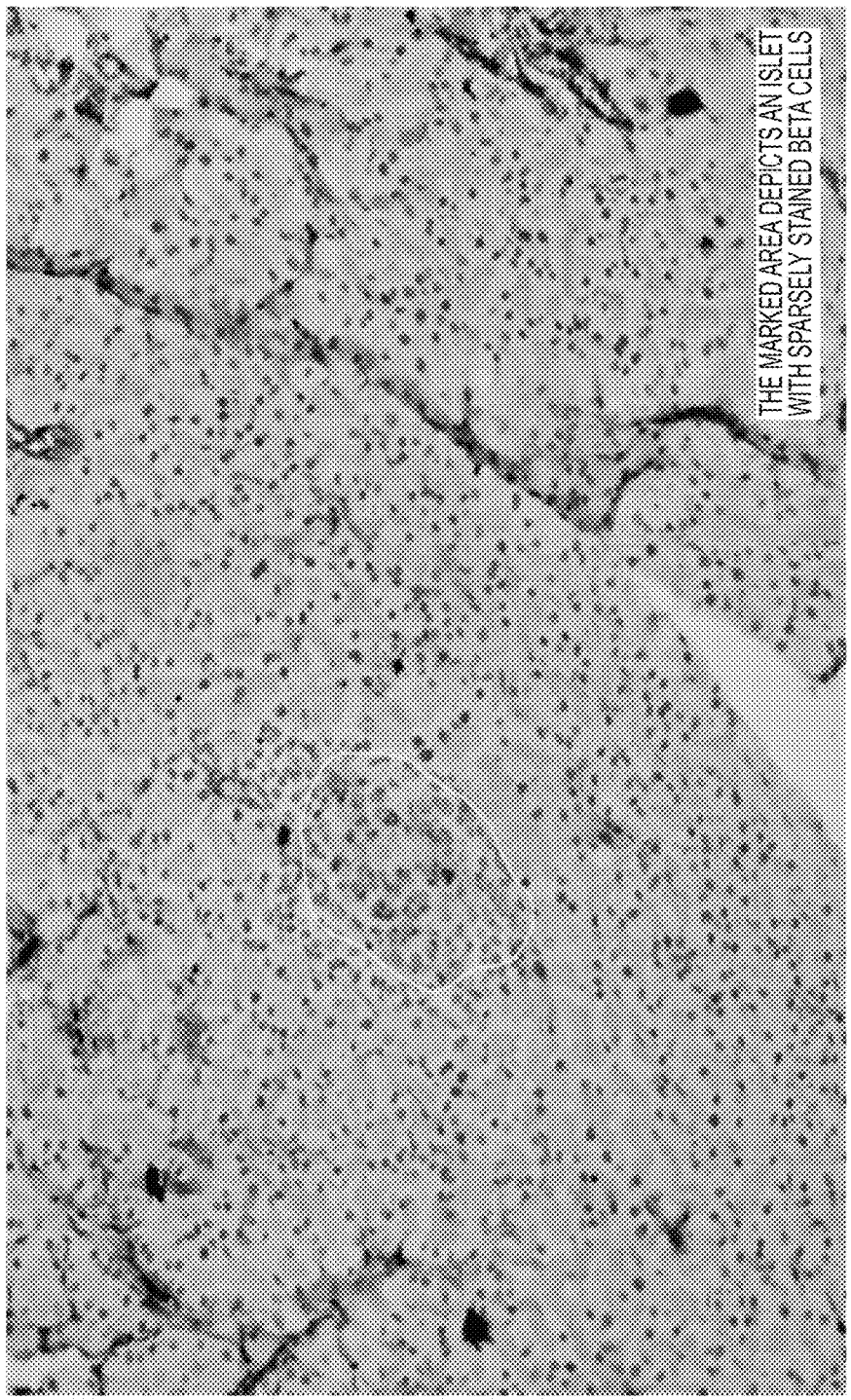

FIG. 14. Histopathological examination of the pancreas of group treated with methanolic extract of fresh leaves of Costus pictus D. Don, the extract had low oxalic acid and/or oxalates content (Sample 2 prepared as per Example 1). The marked area depicts an islet of Langerhans with sparsely stained beta cells.

Figure 15:
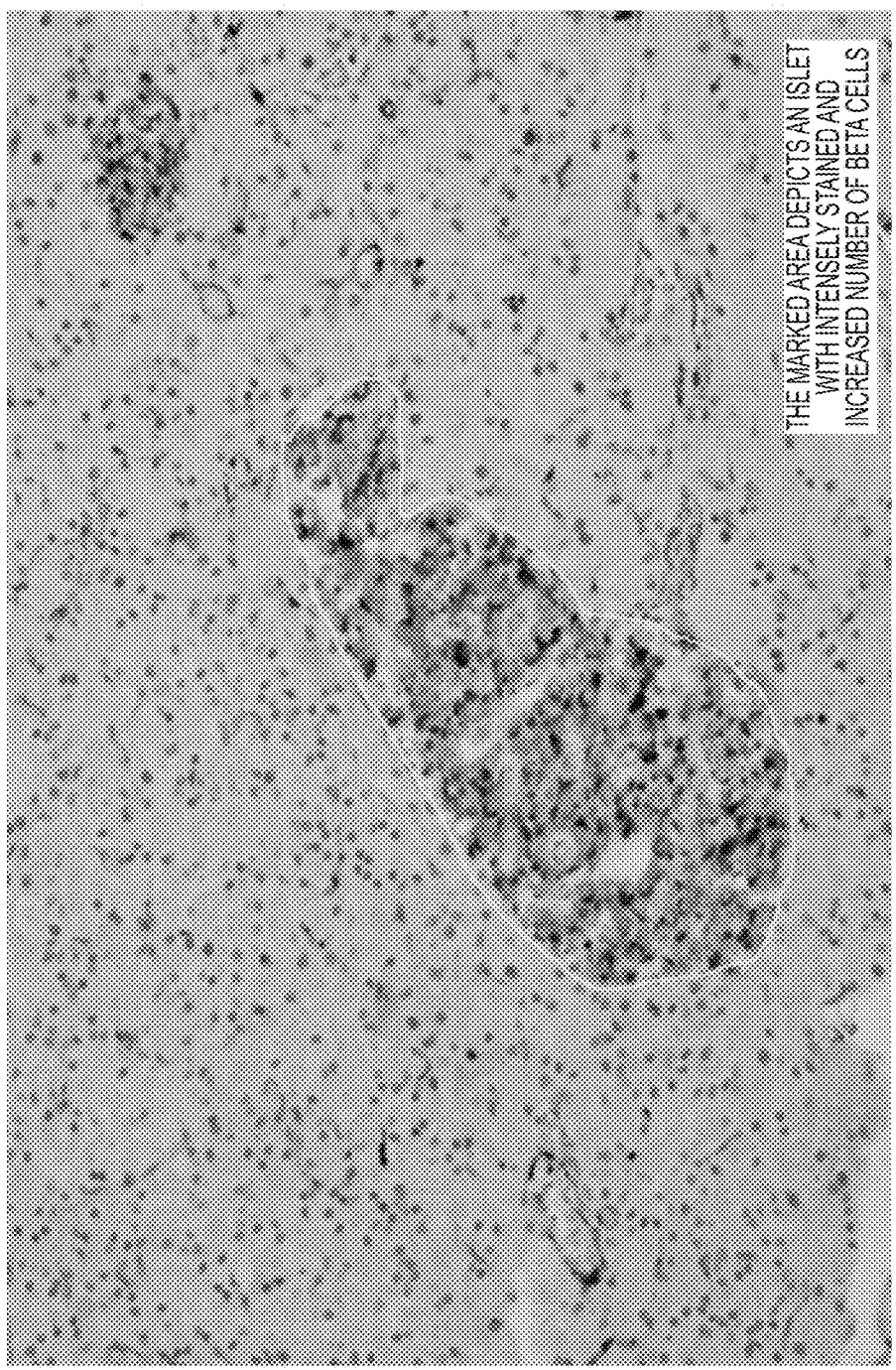

FIG. 15. Histopathological examination of the pancreas of group treated with silica purified ethyl acetate extract of 90% methanolic extract of fresh leaves of Costus pictus D. Don, and the extract had low oxalic acid and/or oxalates content (Sample 5 prepared as per Example 4). The marked area depicts an islet of Langerhans with intensely stained and increased number of beta cells.

Figure 16:
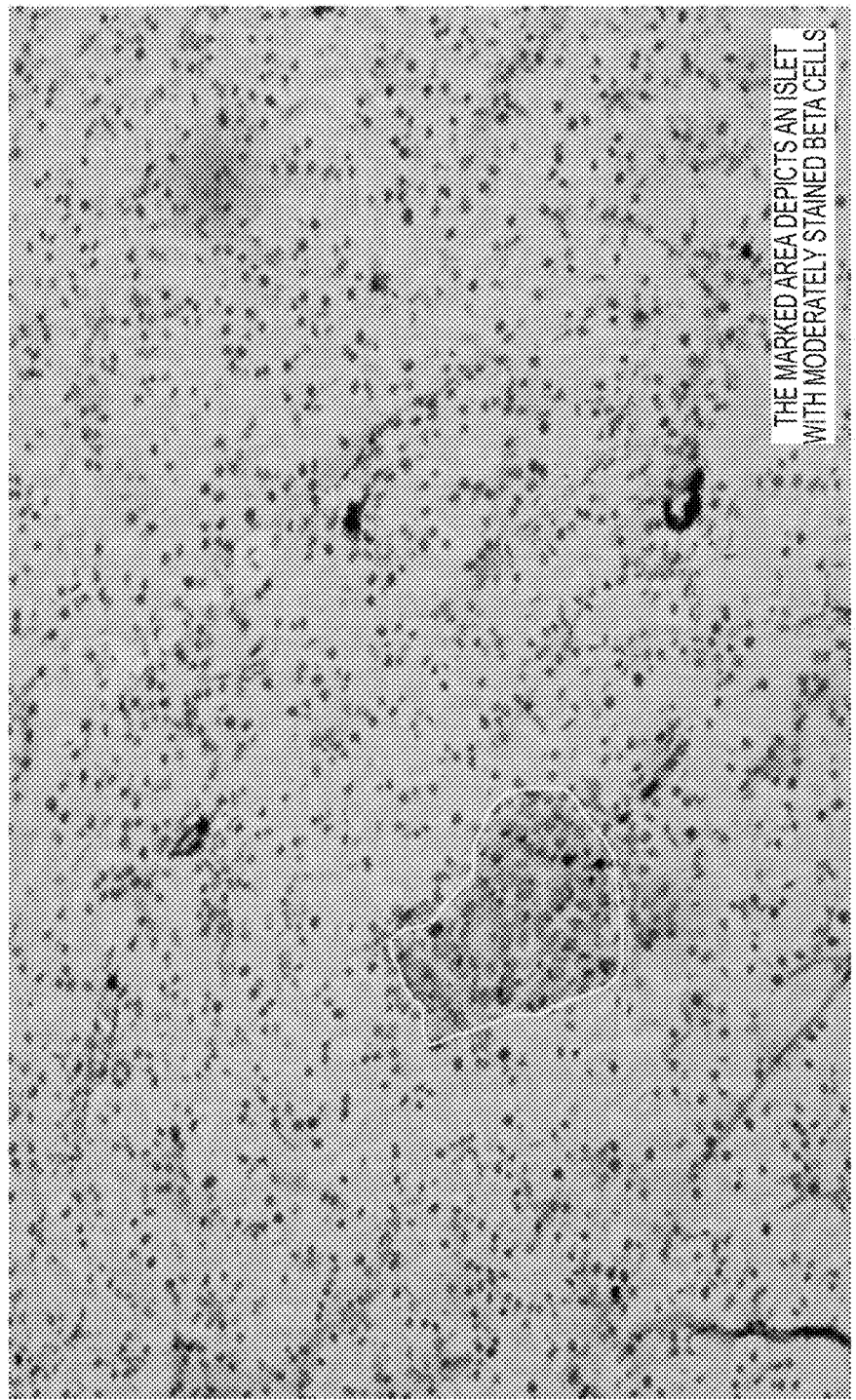

FIG. 16. Histopathological examination of the pancreas of group treated with Ethyl acetate extract of 90% methanol extract of fresh leaves of Costus pictus D. Don, the extract had low oxalic acid and/or oxalates content (Sample 4 prepared as per Example 3). The marked area depicts an islet of Langerhans with moderately stained beta cells.

Figure 17:
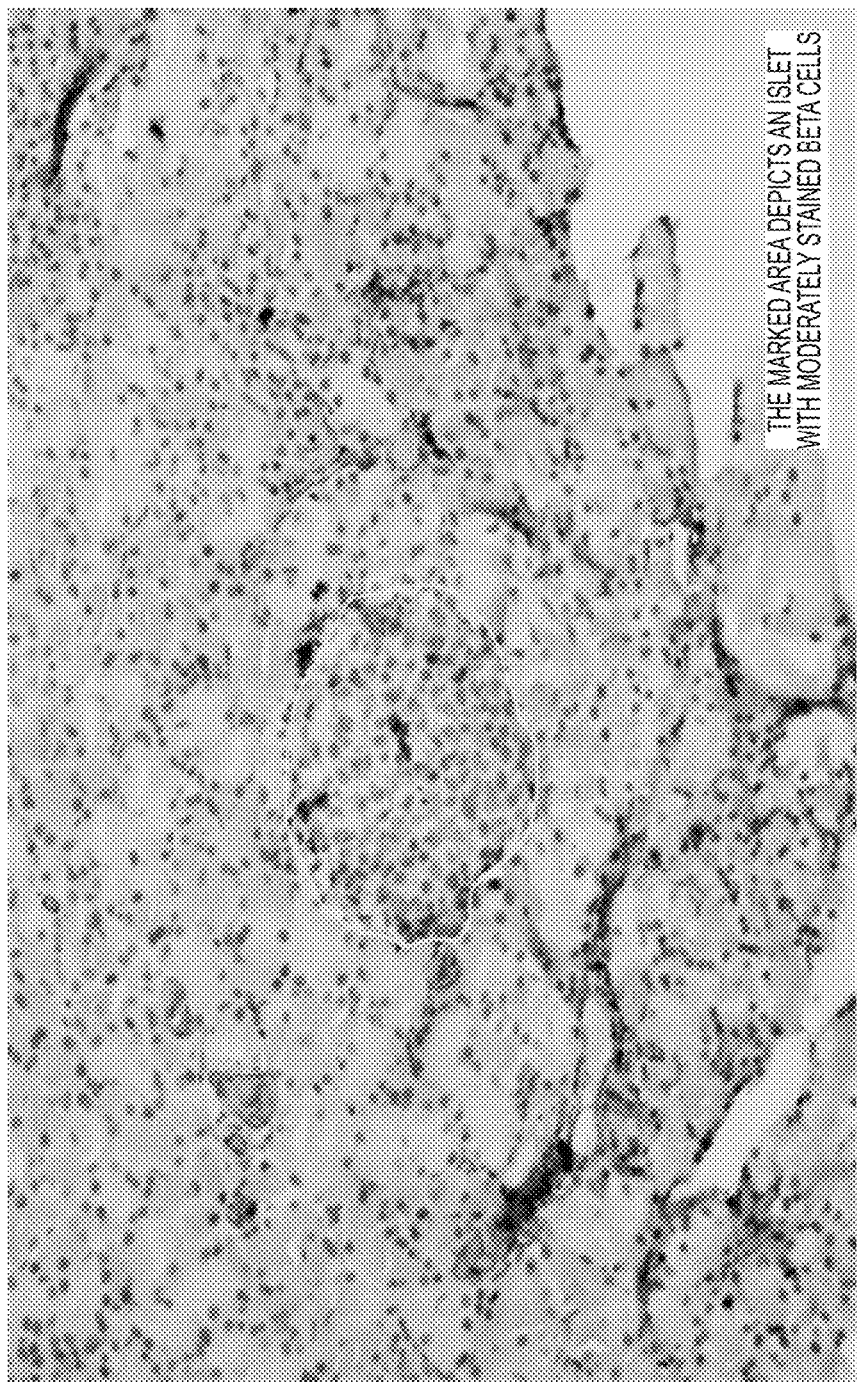

FIG. 17. Histopathological examination of the pancreas of group treated with methanolic extract of fresh leaves of Costus pictus D. Don (Sample 1 prepared as per Example 1). The marked area depicts an islet of Langerhans with moderately stained and increased number of beta cells.

DETAILED DESCRIPTION

The disclosure provides an extract of Costus pictus D. Don having low oxalic acid and/or oxalates content useful for the treatment of diabetes, treatment of dyslipidemia and related conditions. The disclosure also provides composition of Costus pictus D. Don extract having low oxalic acid and/or oxalates content and a method of preparation of an extract of Costus pictus D. Don having low oxalic acid and/or oxalates content.

The present disclosure provides an extract of Costus pictus D. Don having low oxalic acid and/or oxalates content. The extract contains hydroxycinnamic acid derivatives and flavonol mono-, di- and triglycosides along with small amounts of free flavonols. Hydroxycinnamic acid derivatives include caffeic acid, p-coumaric acid, ferulic acid and sinapic acid. The flavonols include free flavonols such as quercetin, kaempferol, isorhamnetin. Flavonols also include glucose derivatives of quercetin, glucose derivatives of kaempferol, glucose derivatives of isorhamnetin, galactose derivatives of quercetin, galactose derivatives of kaempferol, galactose derivatives of isorhamnetin, rhamnose derivatives of quercetin, rhamnose derivatives of kaempferol, and rhamnose derivatives of isorhamnetin. Flavonols include flavonol mono-, di- and triglycosides with sugars such as glucose, galactose and rhamnose. In some embodiments, the constituents of flavonols include small amounts of free flavonols such as quercetin, kaempferol and isorhamnetin.

We found that 90% methanolic extract of Costus pictus D. Don extract has about 56 to 60% oxalic acid and or oxalates.

Costus pictus fresh leaves contain oxalic acid and oxalates. (Oxalic acid and oxalate oxidase enzyme in Costus pictus D. Don, Rajendran Sathishraj, Antoney Augustin, Acta Physiol plant, DOI 10.1007/s 11738-011-0866-x.) Fresh leaves contain 5% w/w oxalic acid and dried leaves contain 1% w/w oxalic acid. The oxalates found in leaves are soluble oxalates (sodium oxalate, potassium oxalate) and insoluble oxalate (calcium oxalate). Soluble oxalates are soluble in methanol and water, but calcium oxalate is not soluble water. (The probable function of calcium oxalate crystals in plants, Alberts Schneider, Chicago journals, Botanical Gazette, Vol. 32, No. 2 (August 1901), pp. 142-144.) Oxalic acid is freely soluble in water. In the disclosed embodiments, when the Costus pictus leaves are extracted with methanol, the methanol extract contains methanol soluble and water soluble oxalates such as sodium oxalate, potassium oxalate, and oxalic acid. The methanol extract is then treated with water and water part (supernatant) is removed to obtain water insoluble part of methanol extract of fresh leaves of Costus pictus. Treatment with water removes sodium oxalate, potassium oxalate, oxalic acid in to the water part (supernatant). The oxalic acid content as analysed by HPLC in methanol extract is 56%, in water insoluble part it is 8% and water part it is 75%. The HPLC analysis for oxalic acid comprises treating the extract with $H_2SO_4$, which again hydrolyses and oxalates present in the extract to liberate free oxalic acid.

Since oxalic acid is found in high concentration in (Costus pictus D. Don and it is found to be toxic, we standardized a method of making Costus pictus D. Don extract with very low level of oxalic acid and or oxalates. The new extract was tested for its anti diabetic action and we found that anti diabetic activity of *Costus pictus* extract did not decrease after reducing the oxalic acid or oxalates content in the extract.

The disclosure provides a dosage form of composition of an extract of *Costus pictus* D. Don having low oxalic acid and/or oxalates content. The disclosure provides a dosage form of composition of an extract of *Costus pictus* D. Don having low oxalic acid and/or oxalates content for oral administration. Dosage forms of the extract are selected from the group consisting of a capsule, tablet, granule, sachet, powder, paste, ointment, infusion, injection, ampoule, solution, suspension, emulsion, pill, sustained release formulation and combinations thereof. In some embodiments, the dosage forms include fillers. Fillers can be lactose, spray dried lactose, starch, dibasic calcium phosphate, tribasic calcium phosphate, microcrystalline cellulose, hydroxy propyl methyl cellulose, calcium carbonate or combinations thereof.

The disclosed composition of extract *Costus pictus* D. Don is useful for the treatment of diabetes, dyslipidemia and is also useful for increasing antioxidant potential in mammal. Mammals include streptozotocin induced diabetic rats and humans. The method of treatment of diabetes mellitus and dyslipidemia includes administering a dose of about 50 mg/kg/day to about 200 mg/kg/day of composition of an extract of *Costus pictus* D. Don having low oxalic acid and/or oxalates content to the streptozotocin induced diabetic rat. The method of treatment of diabetes mellitus and dyslipidemia includes administering a dose of about 500 mg/day to about 2000 mg/day of composition of an extract of C ostus *pictus* D. Don having low oxalic acid and/or oxalates content to a human.

In one embodiment the disclosure provides an extract of *Costus pictus* D. Don having low oxalic acid and/or oxalates content wherein the components can be derived from fresh whole plant, fresh leaves, dried leaves or dried leaf powder, juice of fresh leaves, fresh or dried aerial parts of *Costus pictus* D. Don or combinations thereof.

The disclosure provides constituents of an extract of *Costus pictus* D. Don having low oxalic acid and/or oxalates content wherein the extract is obtained by treatment with low molecular weight alcohols, as such or mixed with water, halogenated hydrocarbons, organic ethers, low molecular weight esters, other organic solvents and low molecular weight ketones.

Low molecular weight alcohols that can be used in preparation of the extract include methanol, ethanol, isopropanol, n-butanol and combinations thereof. Halogenated hydrocarbons that can be used for extract preparation include methylene chloride, ethylene dichloride, chloroform, and combinations thereof. Esters that can be used for extract preparation include methyl acetate, ethyl acetate, propyl acetate, n-butyl acetate and combinations thereof. Ketones that can be used for extract preparation include acetone, methyl ethyl ketone, and combinations thereof. Alkanes that can be used for preparation of the extract include pentane, hexane, heptane, isooctane, and combinations thereof.

Various methods for the preparation of extract of *Costus pictus* D. Don prepared by the extraction of fresh leaves of *Costus pictus* D. Don are provided.

One of the embodiments under the disclosure is the extraction of fresh leaves of *Costus pictus* D. Don with 90% methanol where oxalic acid is removed from the extract by heating the extract with water at 80° C. The resultant dried powder of 90% methanol extract of *Costus pictus* D. Don has low oxalic acid and/or oxalates content. The process steps involved are as under.

Fresh leaves of *Costus pictus* D. Don are extracted with 90% methanol. The mixture is refluxed for one hour to obtain a first residue and supernatant. After first extraction, the first residue is further extracted two more times with four times the quantity of methanol at each time. The residue and supernatants are separated. All the supernatants are pooled and concentrated to form concentrated methanol extract. Concentrated methanol extract is dried to get powder of 90% methanolic extract of *Costus pictus* D. Don. Powder of 90% methanolic extract of *Costus pictus* D. Don is heated with water at 80° C. First residue and water part is obtained and the water part is discarded. First residue is again heated with water at 80° C. Second residue and water part is obtained. While the water part is discarded, second residue is dried to get powder of 90% methanol extract of fresh leaves of *Costus pictus* D. Don. The extract has low oxalic acid and/or oxalates content (8%).

Another embodiment provides method of preparation of purified 90% methanol extract of fresh leaves of *Costus pictus* D. Don. The resulting extract has low oxalic acid and/or oxalates content. Powder of 90% methanol extract of fresh leaves of *Costus pictus* D. Don is dissolved in minimum amount of solvent and silica gel is added in a vessel. Swirl the mixture until the solvent evaporates and passed through a column, which is already wet packed with silica gel and hexane. Then it is eluted with hexane followed by methanol. Methanol fractions are collected and hexane fraction is discarded. Methanol fraction is concentrated and dried to get purified 90% methanol extract of fresh leaves of *Costus pictus* D. Don, and the extract has low oxalic acid and/or oxalates content (3%).

One embodiment provides a method of preparing ethyl acetate extract of 90% methanol extract of fresh leaves of *Costus pictus* D. Don, and the extract has low oxalic acid and/or oxalates content. Fresh leaves of *Costus pictus* D. Don are extracted with 90% methanol to get powder of 90% methanolic extract of *Costus pictus* D. Don. Powder is treated with water and heated at 80° C. to remove the oxalic acid content to get powder of 90% methanol extract of fresh leaves of *Costus pictus* D. Don, and the extract has low oxalic acid and/or oxalates content. Powder of 90% methanol extract of fresh leaves of *Costus pictus* D. Don, and where the extract has low oxalic acid and/or oxalates content, is dissolved in water and is extracted with ethyl acetate and subsequent separation of two phases-aqueous and ethyl acetate. Ethyl acetate part is collected, concentrated and dried to form powder of ethyl acetate extract of 90% methanol extract of *Costus pictus* D. Don. The extract has low oxalic acid and/or oxalates content (1.5%). The water phase is discarded.

Another embodiment provides a method of preparing silica purified ethyl acetate extract of 90% methanol extract of fresh leaves of *Costus pictus* D. Don, wherein the extract has low oxalic acid and/or oxalates content. Ethyl acetate extract of 90% methanol extract of fresh leaves of *Costus pictus* D. Don wherein the extract has low oxalic acid and/or oxalates content is dissolved in minimum amount of hexane and silica gel is added in a vessel. Swirl the mixture until the solvent evaporates and passed through the column, which is already wet packed with silica gel and hexane. Then it is eluted with hexane followed by methanol. Methanol fractions are collected and hexane fraction is discarded. Methanol fractions are concentrated and dried to get purified ethyl acetate extract of 90% methanol extract of fresh leaves of

*Costus pictus* D. Don and the extract has low oxalic acid and/or oxalates content (0.2%).

Some embodiments provide a method of preparing the extract of *Costus pictus* D. Don. The method includes cleaning a starting material of *Costus pictus* D. Don to obtain a cleaned material. The starting material of *Costus pictus* D. Don can be fresh whole plant, fresh leaves, dried leaves or dried leaf powder, juice of fresh leaves, fresh or dried aerial parts of *Costus pictus* D. Don or combinations thereof. Next the cleaned material is cut. Next, the cut material is extracted with a solvent to obtain a residue and a supernatant. The solvent can be water, hexane, methanol, ethanol, isopropanol, n-butanol, methyl acetate, ethyl acetate, propyl acetate, n-butyl acetate or combinations thereof. Supernatant is concentrated and dried to form a dried powder. Dried powder is heated with water at 80° C. to form second residue and second supernatant (water part). Water part contains oxalic acid and oxalates. The heating increases solubility of oxalic acid and oxalates in water. Therefore, decreases oxalic acid and oxalates content in the second residue. Next, the second residue is dried to obtain a dry powder. The dry powder is dissolved in water and extracted with a solvent such as water, hexane, methanol, ethanol, isopropanol, n-butanol, methyl acetate, ethyl acetate, propyl acetate, n-butyl acetate or combinations thereof to obtain aqueous phase and solvent phase. Solvent phase is concentrated and dried to form powder. Powder is mixed with another solvent to form a mixture. Solvent can be water, hexane, methanol, ethanol, isopropanol, n-butanol, methyl acetate, ethyl acetate, propyl acetate, n-butyl acetate or combinations thereof. Silica gel is added to the mixture and resulting product is dried to form dried powder. The dried powder is loaded onto a silica gel column. The silica gel column is eluted with a solvent to obtain an eluate. Solvent can be water, hexane, methanol, ethanol, isopropanol, n-butanol, methyl acetate, ethyl acetate, propyl acetate, n-butyl acetate or combinations thereof. The eluate is concentrated and dried to obtain a dried powder extract of *Costus pictus* D. Don.

Some embodiments provide a method of preparing an extract of *Costus pictus* D. Don. The method includes cleaning a starting material of *Costus pictus* D. Don to obtain a cleaned material. The cleaned material is cut. The cut product is extracted with 90% methanol to form a mixture. The mixture is refluxed at the boiling temperature (60-70° C.) of methanol to obtain a residue and a supernatant. The residue is separated from the supernatant by filtration. The supernatant is concentrated to obtain a concentrated methanol extract. The concentrated methanol extract is dried to obtain a powder of the methanol extract. The dried powder is mixed with water to obtain a mixture. The mixture is heated to obtain a residue and a supernatant. The residue and supernatant are separated. The residue is dried to obtain a dry powder having about 10% of oxalic acid. Some embodiments of the dry powder have less than 10% oxalic acid. Some embodiments of the dry powder have about 8% oxalic acid. Some embodiments of the method further include mixing the dry powder with methanol and silica gel to obtain a mixture. Then evaporating methanol from the mixture to obtain a methanol treated dry powder which includes the extract and silica gel components. The dry powder is loaded onto a wet packed silica gel column to obtain an extract loaded silica gel column. The wet packed silica gel column has silica gel and hexane. The extract loaded silica gel column is eluted with hexane to obtain a silica gel column after hexane elution. The silica gel column eluted with hexane is further eluted with methanol and a methanol eluate fraction is obtained. The methanol eluate fraction is concentrated to form a concentrated extract. The concentrated extract is dried to obtain a dry powder having about 5% oxalic acid. Some embodiments of the dry powder have less than 5% oxalic acid. Some embodiments of the dry powder have about 3% oxalic acid.

Some embodiments provide a method of preparing an extract of *Costus pictus* D. Don. The method includes cleaning a starting material of *Costus pictus* D. Don to obtain a cleaned material. The cleaned material is cut. The cut product is extracted with 90% methanol to form a mixture. The mixture is refluxed at the boiling temperature (60-70° C.) of methanol to obtain a residue and a supernatant. The residue is separated from the supernatant by filtration. The supernatant is concentrated to obtain a concentrated methanol extract. The concentrated methanol extract is dried to obtain a powder of the methanol extract. The dried powder is mixed with water to obtain a mixture. The mixture is heated to obtain a residue and a supernatant. The residue and supernatant are separated. The residue is dried to obtain a dry powder having about 10% of oxalic acid. Some embodiments of the dry powder have less than 10% oxalic acid. Some embodiments further include dissolving the dry powder in water to obtain a mixture. Extracting the mixture with ethyl acetate to obtain an aqueous phase and an ethyl acetate phase. Next concentrating the ethyl acetate phase to obtain a concentrated ethyl acetate extract. Next, drying the ethyl acetate extract under vacuum at above 500 mm of mercury to form a dry powder of the ethyl acetate extract. The dry powder has about 2.5% of oxalic acid. Some embodiments of the dry powder have less than 2.5% oxalic acid. Some embodiments of the dry powder have about 1.5% oxalic acid. Some embodiments of the method further include mixing the dry powder having about 2.5% of oxalic acid with methanol and silica gel to obtain a mixture. Then drying the mixture to obtain a dry powder. Next the dry powder is loaded onto a wet packed silica gel column to obtain an extract loaded silica gel column. The wet packed silica gel column has silica gel column in hexane solvent. The extract loaded silica gel column is eluted with hexane to obtain a silica gel column after hexane elution. The silica gel column eluted with hexane is eluted with methanol and a methanol eluate fraction is obtained. The methanol eluate fraction is concentrated form a concentrated extract. The concentrated extract is dried to obtain a dry powder. Some embodiments of the dry powder have about 1% oxalic acid. Some embodiments of the dry powder have less than 1% oxalic acid. Some embodiments of the dry powder have about 0.2% oxalic acid.

Some embodiments provide a composition having an extract of *Costus pictus* D. Don such as a methanol extract of *Costus pictus* D. Don having about 10% of oxalic acid. Some embodiments provide a composition having an extract of *Costus pictus* D. Don such as a methanol extract of *Costus pictus* D. Don having about 5% of oxalic acid. Some embodiments provide a composition having an extract of *Costus pictus* D. Don such as an ethyl acetate extract of *Costus pictus* D. Don having about 2.5% of oxalic acid. Some embodiments provide a composition having an extract of *Costus pictus* D. Don such as an ethyl acetate extract of *Costus pictus* D. Don having about 1% of oxalic acid. Some embodiments provide an extract of *Costus pictus* D. Don having a total of oxalic acid and oxalates content ranging from about 0.2% to about 10%.

Some embodiments are useful for treatment of diabetes, treatment of dyslipidemia and related conditions by administering extract to a mammal. Mammals include animals and human beings. Some embodiments provide a method of decreasing blood glucose level by administering the extract of *Costus pictus* D. Don. Some embodiments provide a method of decreasing HbAlc (glycosylated hemoglobin) by administering the extract of *Costus pictus* D. Don. Some embodiments provide a method of increasing serum insulin level by administering the extract of *Costus pictus* D. Don. Some embodiments provide a method of increasing liver and muscle glycogen. Some embodiments provide a method of increasing insulin secretaegogue effect. Some embodiments provide a method of treating dyslipidemia. Some embodiments provide a method of decreasing triglycerides level. Some embodiments provide a method of decreasing LDL cholesterol levels. Some embodiments provide a method of decreasing VLDL cholesterol level. Some embodiments provide a method of increasing HDL cholesterol level. Some embodiments provide a method for increasing anti oxidant potential. Some embodiments provide method of decreasing TBARS level (Thiobarbituric acid reactive substances). Some embodiments provide a method of increasing SOD level (Superoxide dismutase). Some embodiments provide a method of increasing catalase level. Some embodiments provide a method of increasing GSH level (Glutathione). Some embodiments provide a method of increasing GPx (glutathione peroxidase) level. Some embodiments provide a method for regeneration of pancreatic beta cells.

Extract of *Costus pictus* D. Don having low oxalic acid content containing hydroxycinnamic acid derivatives and flavonol mono-, di- and triglycosides along with small amounts of free flavonols are identified by HPLC and LCMS analysis.

The extract of *Costus pictus* D. Don is analyzed by HPLC for the presence of hydroxy cinnamic acid and flavonoids.

Figure 1:
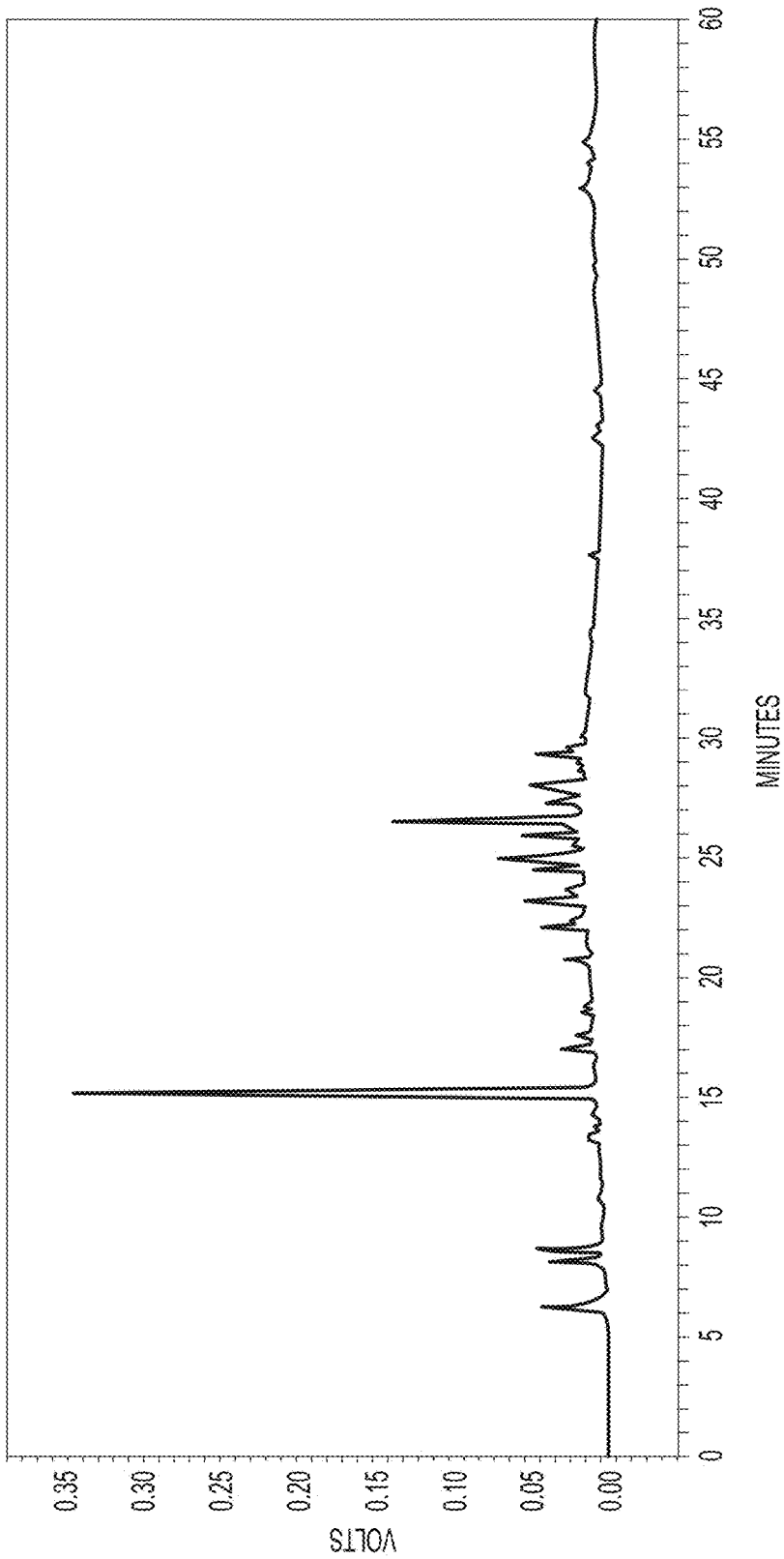
FIG. 1 shows chromatogram peaks corresponding to hydroxycinnamic acid derivatives at 254 nm on High performance liquid chromatography (HPLC) of a 90% methanol extract of fresh leaves of Costus pictus D. Don, and wherein the extract had low oxalic acid and/or oxalates content (sample 2 prepared as per example 1).
Figure 2:
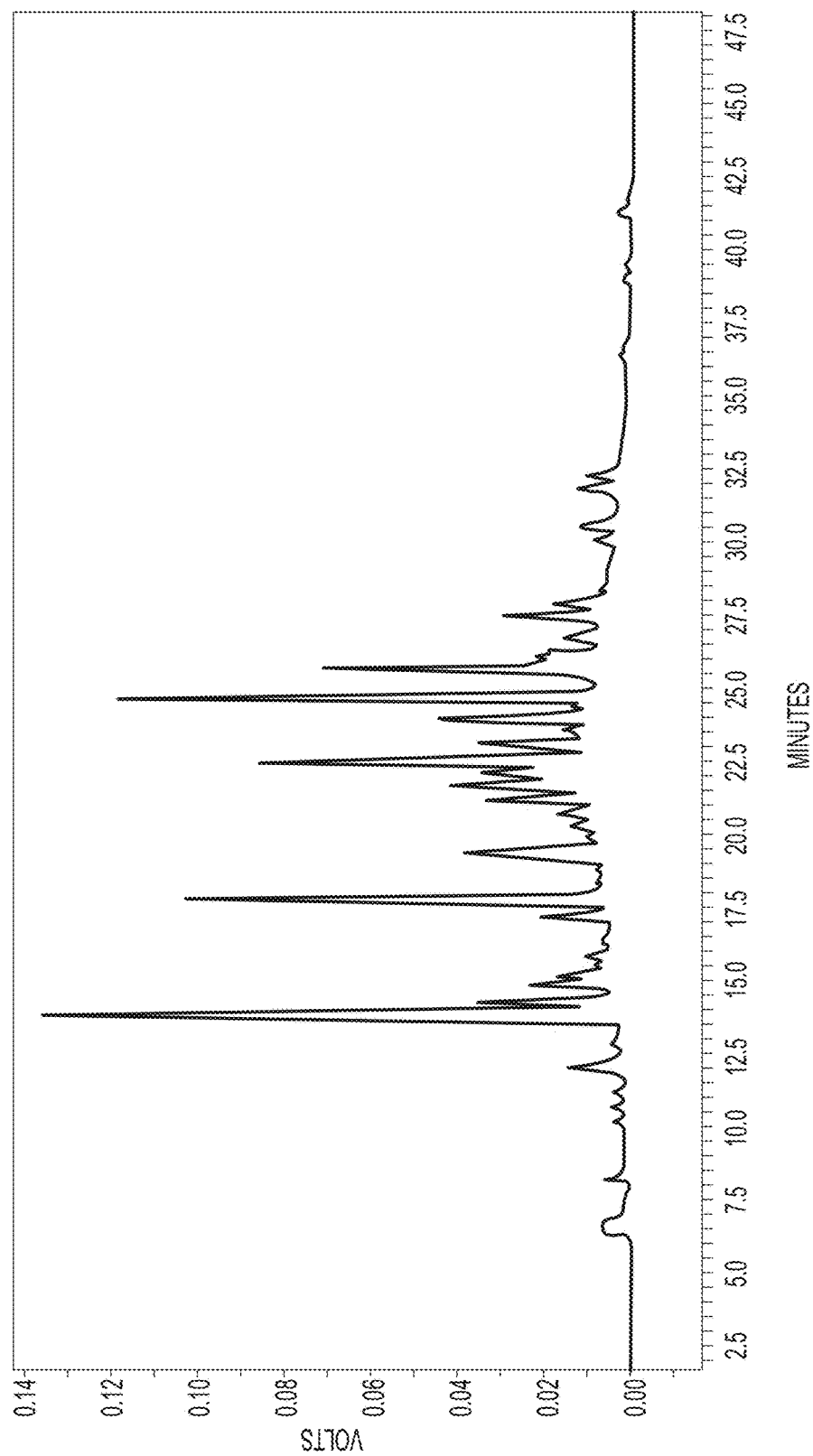
FIG. 2 shows peaks corresponding to flavonoids on High performance liquid chromatography (HPLC) chromatogram at 324 nm of a 90% methanol extract of fresh leaves of Costus pictus D. Don, wherein the extract had low oxalic acid and/or oxalates content (sample 2 prepared as per example 1).

The UV data at 254 nm (FIG. 1) shows several peaks corresponding to hydroxycinnamic acid. UV data at 324 nm (FIG. 2) shows several peaks which corresponding to flavonoids. Alkali hydrolysis and acid hydrolysis of the extract of *Costus pictus* D. Don confirm the presence of hydroxycinnamic acids and flavonoids respectively. The HPLC analysis of alkali hydrolysed extract of *Costus pictus* D. Don detects hydroxycinnamic acid at 324 nm. Accordingly, p-coumaric acid, caffeic acid, ferulic acid and sinapic acid are identified after alkali hydrolysis of the extract (FIG. 3) by co-injection with reference standards.

HPTLC finger print (FIG. 4a and FIG. 4b) of *Costus pictus* D. Don extract after hydrolysis shows the presence of p-coumaric acid, caffeic acid, ferulic acid and sinapic acid (Track 5) against reference standards ferulic acid (Track 1), Sinapic acid (Track 2), p-coumaric acid (Track 4) and caffeic acid (Track 5).

Figure 5:
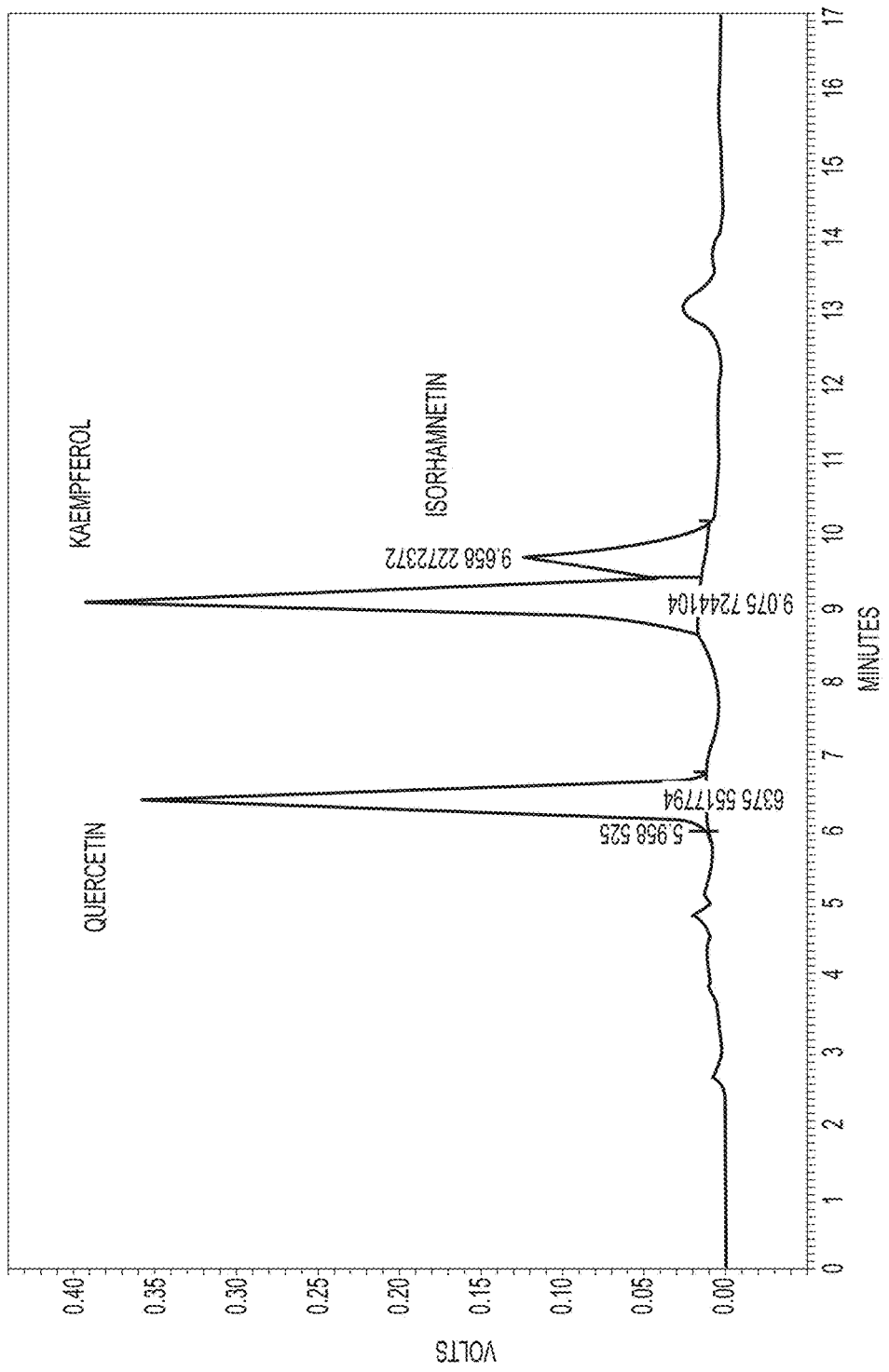
FIG. 5. shows flavonols (quercetin, kaempferol and isorhamnetin) peaks detected at 368 nm on High performance liquid chromatography (HPLC) analysis of acid hydrolysed 90% methanol extract of fresh leaves of Costus pictus D.

Similarly HPLC analysis of acid hydrolysed extract of *Costus pictus* detects flavonoids and the three peaks detected at 368 nm (FIG. 5) and these corresponds to quercetin, kaempferol and isorhamnetin as confirmed by co-injection with reference standards.

HPTLC finger print (FIG. 6a and FIG. 6b) of aqueous layer of *Costus pictus* D. Don extract after acid hydrolysis shows the presence of sugars like glucose, galactose and rhamnose (Track 4) against reference standards Glucose (Track 1), Ribose (Track 2), D-Galactose (Track 3), D-fructose (Track 4) and D-Rhamnose (Track 7).

The extract of *Costus pictus* D. Don is subjected to liquid chromatography-mass spectrometry (LCMS) analysis. The chromatograms at 324 nm and 370 nm correspond to hydroxycinnamic acid derivatives and flavonoid glycosides respectively.

The LCMS chromatogram at 324 nm (FIG. 9) clearly shows a number of components, mainly hydroxycinnamic acid derivatives and these could be identified from the MS data (Table 4).

In the same way flavonoids are detected at 370 nm by LCMS (FIG. 10). The data shows the presence of several flavonoid derivatives and these could be detected and identified. (Table 5)

It will be readily understood by the skilled artisan that numerous alterations may be made to the examples and instructions given herein including alternate compositions without departing from either the spirit or scope of the present invention. These and other objects and features of present invention will be made apparent from the following examples. The following examples as described are not intended to be construed as limiting the scope of the present invention.

EXAMPLE 1

Fresh leaves of *Costus pictus* D. Don were collected (5000 Kg). Fresh leaves were cleaned and cut into small pieces. 90°/o methanol in an amount four times the quantity of fresh leaves of *Costus pictus* D. Don was added to fresh leaves for methanol extraction. The extraction was performed using an extractor with reflux condenser. The bottom of the extractor was fitted with a polypropylene (100 microns) filter cloth. The mixture was refluxed at the boiling temperature (60-70° C.) of methanol for one hour to obtain a first residue and supernatant. The first residue was then further extracted two more times with four times the quantity of methanol at each time. The residue and supernatants were separated by draining out the supernatant from the extractor bottom through the polypropylene filter cloth using a centrifugal pump. All the supernatants were pooled and concentrated in an Agitated thin film evaporator (ATFE) to form a concentrated methanol extract. The concentrated methanol extract was dried under vacuum at above 500 mm of mercury to get dry powder of 90% methanol extract of fresh leaves of *Costus pictus* D. Don (Yield 125 Kg). (sample 1). Now the oxalic acid content in 90% methanolic extract of *Costus pictus* D. Don is 56%.

Powder of 90% methanolic extract of *Costus pictus* (75 Kg of sample 1) was heated with water to form a residue and a supernatant (water part). Discard the water part. Residue was again treated with water and heat to form another residue and supernatant. Residue was dried under vacuum at above 500 mm of mercury to obtain a dry powder. The yield of the powder was 34 kg from a starting material of 75 kg. This powder was referred to as powder of 90% methanol extract of *Costus pictus* D. Don. This extract has low oxalic acid and/or oxalates content. (Sample 2). The oxalic acid content in 90% methanolic extract of *Costus pictus* D. Don is only 8%.

Analysis of Oxalic Acid by HPLC

Oxalic acid was estimated by high performance liquid chromatography (HPLC-DAD) on a C18 column (250×4.6 mm, Gemini 5 µm, USA.). The mobile phase was 5 mM $H_2SO_4$ and used under isocratic condition with an eluent flow rate of 1 mL/min. Oxalic acid was detected at 210 nm.

Standard was prepared by weighing 5 mg of standard oxalic acid (95% purity) and was made up to 50 ml with 6 mM $H_2SO_4$. Sample was prepared by weighing 50 mg of the dry extract of *Costus pictus* and was made up to 50 ml with 6 mM $H_2SO_4$. Both the sample and standard were filtered separately through a 0.2 µm membrane filter before injection into the HPLC column. The injection volume was 20 µl.

Oxalic acid was detected at 210 nm. By comparing the area of standard and sample, the percentage of oxalic acid present in the sample was quantified.

Oxalic acid % =
$$\frac{\text{Area of sample} \times \text{amount of standard}}{\text{Amount of sample} \times \text{Area of standard}} \times \text{purity of standard}$$

HPLC Analysis 50 mg of the Sample 2 was weighed and transferred into 50 mil standard flask and dissolved in methanol and made up to the mark using methanol.

The Sample 2 dissolved in methanol was analyzed on a Shimadzu Prominence HPLC using a Phenomenex C-18 column (250×4.6 mm), 5μ, RT (25° C.).

A gradient elution using solvents 5% ACN (acetonitrile) in water (solvent A) and 95% ACN (acetonitrile) in water (solvent B) having 5 mM ammonium acetate (pH 4) was used. The composition of solvent B was changed from 5% to 50 in 35 min, then to 80% in 45 min and maintained at 80% till 55 min and then maintained at 5% from 56 to 60 min. A UV detector at 254 nm and 324 nm was used to collect the data.

The UV data at 254/324 nm shows several peaks which correspond to hydroxycinnamic acid derivatives and flavonoids. Alkali hydrolysis and acid hydrolysis confirmed the presence of hydroxycinnamic acids and flavonoids respectively.

Acid Hydrolysis 150 g of Sample 2 was weighed and transferred into a glass lined vessel. Then Sample 2 was dissolved in 3.75 L of water and 562.5 mil concentrated hydrochloric acid was added to the vessel and was refluxed for 3 hours. The contents of the vessel were cooled and transferred into a liquid-liquid extractor and extracted with ethyl acetate. Ethyl acetate phase and aqueous phase were separated and ethyl acetate phase was collected. Ethyl acetate phase was transferred into the liquid-liquid extractor and extracted with water until the pH of water became neutral. Ethyl acetate phase and aqueous phase were separated and ethyl acetate phase was collected and concentrated in an Agitated thin film evaporator (ATFE) to form concentrated ethyl acetate extract. Ethyl acetate concentrate was fed into vacuum stripper and dried under vacuum at above 500 mm of mercury to form acid hydrolysis product of water treated 90% methanol extract of fresh leaves of Costus pictus D. Don (yield 75 g).

50 mg of the acid hydrolysis product (ethyl acetate concentrate) was accurately weighed and transferred into a 50 ml standard flask and dissolved in methanol and made up to the mark using methanol.

The dissolved sample was analysed on a Shimadzu Prominence HPLC. Column: Thermo Betasil. C18, 250×4.6 mm, 5μ, Solvent system (isocratic): Methanol-Acetonitrile-Water (40:15:45 v/v/v) containing 1% acetic acid, flow rate 1 ml/min, detection at 368 nm.

Three peaks were detected at 368 nm and these corresponded to quercetin, kaempferol and isorhamnetin as confirmed by co-injection with reference standards.

Alkali Hydrolysis 150 g of 90% methanol extract of fresh leaves of Costus pictus D. Don, which has low oxalic acid and/or oxalates content (Sample 2) was weighed. 6 L of 2 M NaOH was added and the mixture was transferred into an agitator vessel. The mixture was heated at 40° C. for half an hour with constant stirring. After half an hour the mixture was cooled and pH of the mixture was adjusted to 3 by adding concentrated HCl. The mixture was transferred into a liquid-liquid extractor and ethyl acetate was added. Ethyl acetate phase and aqueous phase were separated and ethyl acetate phase was collected and concentrated in an Agitated thin film evaporator (ATFE) to form concentrated ethyl acetate extract. The concentrated ethyl acetate extract was fed into vacuum stripper and dried under vacuum at above 500 mm of mercury to form alkali hydrolysis product of water treated 90% methanol extract of fresh leaves of Costus pictus D. Don (yield 75 g).

50 mg of the alkali hydrolysis product was accurately weighed and transferred into a 50 ml standard flask. Next the alkali hydrolysis product was dissolved in methanol and the flask was made up to the mark using methanol. The dissolved sample was analyzed by HPLC, Column: Thermo Betasil, C18, 250×4.6 mm. S p. Solvent system: Solvent A—1% acetic acid in water, solvent B—1% acetic acid/water/acetonitrile (2:68:30). Gradient: 0 min. 7% solvent B increased to 90% solvent B. Flow rate 1 ml/min. Hydroxycinnamic acids were detected by HPLC at 324 nm and identified by co-injection with reference standards. Accordingly, p-coumaric acid, caffeic acid, ferulic acid and sinapic acid were identified after alkali hydrolysis of the extract.

EXAMPLE 2

30 Kg of Sample 2 was dissolved in minimum amount of methanol and about 30 Kg of silica gel was added in vessel. The mixture was swirled until the methanol evaporated and only a dry powder remained. The dried powder was transferred in to the top of the column, which was already wet packed with silica gel (50 Kg) and hexane. Column was initially eluted with hexane followed by methanol. Methanol fractions were collected and hexane fractions were discarded. Methanol fraction was concentrated in an Agitated thin film evaporator (ATFE) to form concentrated extract. Concentrate was fed into vacuum stripper and dried under vacuum at above 500 mm of mercury to get dry powder. The yield of the powder was 430 g from a starting material of 30 kg. This powder was referred to as powder of silica purified 90% methanol extract of Costus pictus D. Don. The extract has low oxalic acid and/or oxalates content [Sample 3]. Oxalic acid content in silica purified 90% methanolic extract of Costus pictus D. Don was 3%. Oxalic acid was analyzed as in Example 1.

HPLC Analysis

HPLC analysis of Sample 3 was conducted as described in Example 1. The UV data at 254/324 nm shows several peaks which correspond to hydroxycinnamic acid derivatives and flavonoids. Alkali hydrolysis and acid hydrolysis confirmed the presence of hydroxycinnamic acids and flavonoids respectively.

Acid Hydrolysis 150 g of Sample 3 was weighed and Acid hydrolysis was conducted as shown in Example 1. The final product was acid hydrolysis product of purified 90% methanol extract of fresh leaves of Costus pictus D. Don (yield 75 g).

The acid hydrolysis product of purified 90% methanol extract of fresh leaves of Costus pictus D. Don was analysed by HPLC as in Example 1.

Three peaks were detected at 368 nm and these corresponded to quercetin, kaempferol and isorhamnetin as confirmed by co-injection with reference standards.

Alkali Hydrolysis 150 g of Sample 3 was weighed and alkali hydrolysis was conducted as shown in Example 1. The final product was alkali hydrolysis product of purified 90% methanol extract of fresh leaves of *Costus pictus* D. Don (yield 75 g).

The alkali hydrolysis product was analysed by HPLC as in Example 1. Hydroxycinnamic acids were detected at 324 nm and identified by co-injection with reference standards. Accordingly, p-coumaric acid, caffeic acid, ferulic acid and sinapic acid were identified after alkali hydrolysis of the extract.

EXAMPLE 3

3000 Kg of fresh leaves of *Costus pictus* D. Don were extracted with 90% methanol as in Example 1. The product obtained was dry powder of 90% methanol extract of fresh leaves of *Costus pictus* D. Don (Yield 75 Kg).

Oxalic acid was removed from the powder of 90% methanolic extract of *Costus pictus* by a method described in Example 1. The yield of the powder obtained was 34 kg from a starting material of 75 kg. This powder was referred to as powder of 90% methanol extract of *Costus pictus* D. Don and the extract has low oxalic acid and/or oxalates content. Oxalic acid content was about 8%.

The above obtained powder was dissolved in water and transferred into a liquid-liquid extractor and extracted with ethyl acetate. Two phases were formed-aqueous and ethyl acetate. Ethyl acetate phase was collected and aqueous phase was again treated with ethyl acetate two more times in the liquid-liquid extractor and at each time ethyl acetate phase was collected. All the ethyl acetate phase were combined and concentrated in an Agitated thin film evaporator (ATFE) to form concentrated ethyl acetate extract. Ethyl acetate concentrate was fed into vacuum stripper and dried under vacuum at above 500 mm of mercury to form dry powder. The yield of the powder was 30 kg from a starting material of 34 kg. This powder was referred to as powder of ethyl acetate extract of 90% methanol extract of *Costus pictus* D. Don. The extract had low oxalic acid and/or oxalates content (Sample 4). Oxalic acid content in ethyl acetate extract of 90% methanolic extract of *Costus pictus* D. Don was 1.5%. Oxalic acid was analyzed as in Example 1.

HPLC Analysis

The HPLC analysis of Sample 4 was conducted as in Example 1. The UV data at 254/324 nm shows several peaks which correspond to hydroxycinnamic acid derivatives and flavonoids. Alkali hydrolysis and acid hydrolysis confirmed the presence of hydroxycinnamic acids and flavonoids respectively.

Acid Hydrolysis

The acid hydrolysis of sample 4 was conducted as shown in Example 1. The product obtained was acid hydrolysis product of ethyl acetate extract of 90% methanol extract of fresh leaves of *Costus pictus* D. Don (yield 75 g).

The acid hydrolysis product was analysed by HPLC as in Example 1. Three peaks were detected at 368 nm and these corresponded to quercetin, kaempferol and isorhamnetin as confirmed by co-injection with reference standards.

Alkali Hydrolysis

The alkali hydrolysis was conducted as shown in Example 1 by using 150 g of sample 4. The product obtained was alkali hydrolysis product of ethyl acetate extract of 90% methanol extract of fresh leaves of *Costus pictus* D. Don (yield 75 g) and it was analysed by HPLC as in Example 1.

Hydroxycinnamic acids were detected at 324 nm and identified by co-injection with reference standards. Accordingly, p-coumaric acid, caffeic acid, ferulic acid and sinapic acid were identified after alkali hydrolysis of the extract.

EXAMPLE 4

25 Kg of sample 4 was dissolved in minimum amount of methanol and about 25 Kg of silica gel was added in a vessel. The mixture was swirled until the methanol evaporated and only a dry powder remained. The Dried powder was transferred into the top of the column, which was already wet packed with silica gel (50 Kg) and hexane. Column was initially eluted with hexane followed by methanol. Methanol fractions were collected and hexane fraction was discarded. Methanol fraction was concentrated in an Agitated thin film evaporator (ATFE) to form concentrated extract. Concentrate was fed into vacuum stripper and dried under vacuum at above 500 mm of mercury to get dry powder. The yield of the powder was 245 g from a starting material of 25 kg. This powder was referred to as powder of purified ethyl acetate extract of 90% methanol extract of *Costus pictus* D. Don. The extract had low oxalic acid and/or oxalates content (Sample 5). Oxalic acid content in purified ethyl acetate extract of 90% methanolic extract of *Costus pictus* D. Don was 0.2%.

Oxalic acid was analyzed as in Example 1.

HPLC Analysis

HPLC analysis of sample 5 was conducted as in Example 1. The UV data at 254/324 nm shows several peaks which correspond to hydroxycinnamic acid derivatives and flavonoids. Alkali hydrolysis and acid hydrolysis confirm the presence of hydroxycinnamic acids and flavonoids, respectively.

Acid Hydrolysis 150 g of Sample 5 was subjected to acid hydrolysis as shown in Example 1. 75 g of acid hydrolysis product of purified ethyl acetate extract of 90% methanol extract of fresh leaves of *Costus pictus* D. Don was obtained.

The acid hydrolysis product was analysed by HPLC as in Example 1. Three peaks were detected at 368 nm and these corresponded to quercetin, kaempferol and isorhamnetin as confirmed by co-injection with reference standards.

Alkali Hydrolysis

Alkali hydrolysis of sample 5 was conducted as in Example 1.75 g of alkali hydrolysis product of purified ethyl acetate extract of 90% methanol extract of fresh leaves of *Costus pictus* D. Don was obtained. Alkali hydrolysis product was analysed by HPLC as in Example 1. Hydroxycinnamic acids were detected at 324 nm and identified by co-injection with reference standards. Accordingly, p-coumaric acid, caffeic acid, ferulic acid and sinapic acid were identified after alkali hydrolysis of the extract.

EXAMPLE 5

Hydroxycinnamic acids are non-flavonoid phenolics characterized by the C6-C3 structure (Table 1). These compounds are abundant in plants and are used in both structural and chemical plant defense strategies. Derivatives of cinnamic acid are present in numerous vegetables and fruits. In *Costus pictus* D. Don extract p-coumaric, caffeic, ferulic and sinapic acids are found in conjugation with sugar or other hydroxycinnamic acids or quinic acid ($R_3$).

TABLE 1

Structure of different hydroxycinnamic acid derivatives present in extract of *Costus pictus* D. Don.

| Hydroxycinnamic acids | $R_1$ | $R_2$ | $R_3$ |
|---|---|---|---|
| p-Coumaric | H | H | H |
| Caffeic | OH | H | H |
| Ferulic | $OCH_3$ | H | H |
| Sinapic | $OCH_3$ | $OCH_3$ | H |

R1 is hydrogen (H), hydroxyl (OH), methoxy($OCH_3$) group depends on the hydroxycinnamic acid present in the extract of *Costus pictus* D. Don.

R2 is hydrogen (H), methoxy ($OCH_3$) depends on the hydroxycinnamic acid present in the extract of *Costus pictus* D. Don.

R3 is hydrogen (H) in all the four hydroxycinnamic acid present in the extract of *Costus pictus* D. Don.

Flavonoids are plant pigments widely distributed in nature. They are polyphenolic compounds comprising fifteen carbons with two aromatic rings connected by a three-carbon bridge, hence C6-C3-C6 (Table 2). They are present in high concentrations in the epidermis of leaves and fruits and have important and varied roles as secondary metabolites, being involved in processes like UV protection, pigmentation, stimulation of nitrogen-fixing nodules and disease resistance. Flavonols are the most widespread of the flavonoids. Quercetin, kaempferol and isorhamnetin, the main flavonols in *Costus pictus* D. Don extract, are found as O-glycosides and as free flavonols. Conjugation occurs most frequently at the 3 position of the C-ring, but substitutions can also occur at the 5, 7, 4', 3' and 5' positions. Mono- di- and triglycosides containing glucose/galactose and rhamnose are found.

| Flavonols | $R_1$ | $R_2$ | $R_3$ |
|---|---|---|---|
| Kaempferol | OH | H | H |
| Quercetin | OH | OH | H |
| Isorhamnetin | OH | $OCH_3$ | H |

R1 is hydroxyl group (OH) in thee flavonols present in the extract of *Costus pictus* D. Don.
R2 is hydrogen (H), hydroxyl (OH), methoxy ($OCH_3$) depends on the flavonols present in the extract of *Costus pictus* D. Don.
R3 is hydrogen (H) in the structure of the flavonols present in the extract of *Costus pictus* D. Don.

High Performance Liquid Chromatography (HPLC) Analysis

The extract of *Costus pictus* was analyzed by HPLC for the presence of hydroxyl cinnamic acid and flavonoids.

The extract was analyzed on a Shimadzu Prominence HPLC using a Phenomenex C-18 column (250×4.6 mm), 5μ, RT (25° C.), Sample concentration—1 mg/ml dissolved in MeOH:Water (1:1).

A gradient elution using solvents 5% ACN (acetonitrile) in water (solvent A) and 95% ACN (acetonitrile) in water (solvent 13) having 5 mM ammonium acetate (pH 4) was used. The composition of B was changed from 5% to 50 in 35 min, then to 80% in 45 min and maintained at 80% till 55 min and then maintained at 5% from 56 to 60 min. A UV detector at 254 nm and 324 nm was used to collect the data.

The UV data at 254 nm (FIG. 1) shows several peaks corresponding to hydroxycinnamic acid. UV data at 324 nm (FIG. 2) shows several peaks which correspond to flavonoids. Alkali hydrolysis and acid hydrolysis confirm the presence of hydroxycinnamic acids and flavonoids, respectively.

Alkali Hydrolysis

Figure 3:
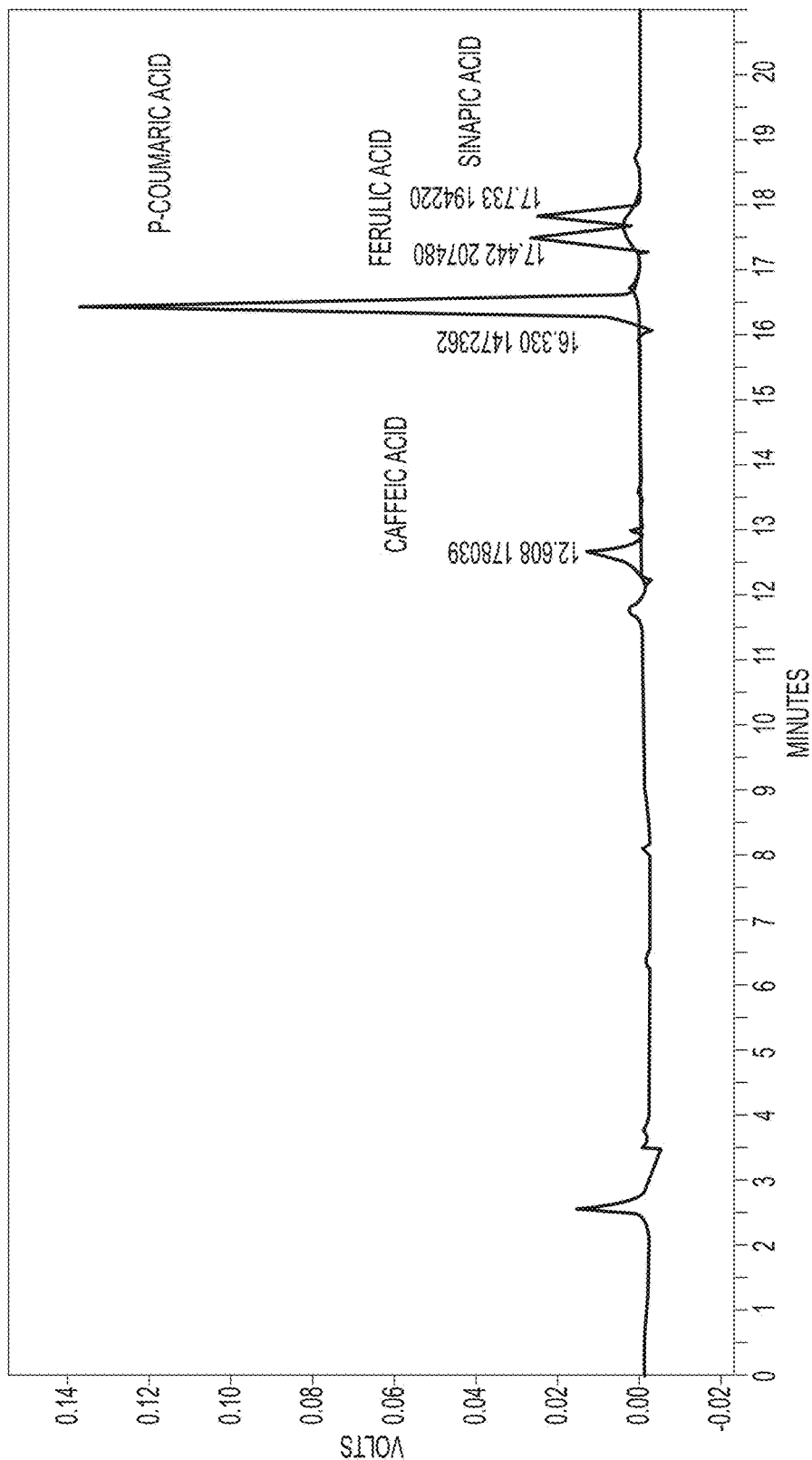
FIG. 3. Provides High performance liquid chromatography (HPLC) data of alkali hydrolysis product of 90% methanol extract (having low oxalic acid and/or oxalates content) of fresh leaves of Costus pictus D. Don (sample 2 prepared as per example 1) in which hydroxycinnamic acids (p-coumaric acid, caffeic acid, ferulic acid and sinapic acid) were detected at 324 nm and identified by co-injection with reference standards.

Alkali hydrolysis was carried out with 2M sodium hydroxide at 40° C. for half-an-hour, acidified with HCl to pH 3 and extracted with ethyl acetate, concentrated and dried under vacuum. Hydroxycinnamic acids were detected by high performance liquid chromatography (HPLC) at 324 nm and identified by co-injection with reference standards. Accordingly, p-coumaric acid, caffeic acid, ferulic acid and sinapic acid were identified after alkali hydrolysis of the extract (FIG. 3). This indirectly confirms the presence of derivatives of these acids in *Costus pictus* D. Don.

HPLC conditions: —Column: Thermo Betasil, C18, 250× 4.6 mm, 5μ. Solvent system: Solvent A—1% acetic acid in water, solvent B—1% acetic acid/water/acetonitrile (2:68:30). Gradient: 0 min. 7% B increased to 90% B. Flow rate 1 ml/min. Detection at 320 nm.

Figure 4B:
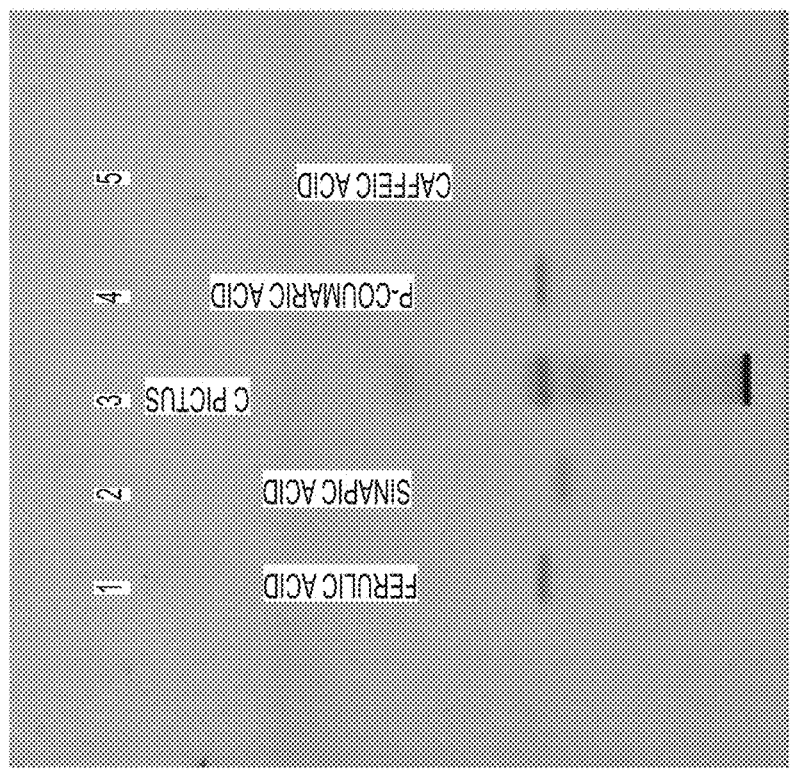
FIG. 4b—provides fingerprinting shows the presence of p-coumaric acid, caffeic acid, ferulic acid and sinapic acid at in visible UV light on HPTLC of alkali hydrolysed 90% methanol extract of fresh leaves of Costus pictus D. Don (sample 2 prepared as per example 1), the extract had low oxalic acid and/or oxalates content.
Figure 4A:
FIG. 4a. provides HPTLC finger print in visible light of 90% methanol extract (having low oxalic acid and/or oxalates content) of fresh leaves of Costus pictus D. Don (sample 2 prepared as per example 1) after alkali hydrolysis shows the presence of p-coumaric acid, caffeic acid, ferulic acid and sinapic acid.

HPTLC finger print of *Costus pictus* D. Don after alkali hydrolysis is shown in FIGS. 4a and 4b. FIG. 4a provides HPTLC finger print of *Costus pictus* D. Don extract after alkali hydrolysis in visible light and FIG. 4b provides HPTLC finger print of *Costus pictus* D. Don extract after alkali hydrolysis in UV light.

HPTLC finger print (FIG. 4a and FIG. 4b) of *Costus pictus* extract after alkali hydrolysis shows the presence of p-coumaric acid, caffeic acid, ferulic acid and sinapic acid (Track 5) against reference standards ferulic acid (Track 1). Sinapic acid (Track 2), p-coumaric acid (Track 4) and caffeic acid (Track 5).

Acid Hydrolysis

Acid hydrolysis was carried out by refluxing with IN HCl for 4 hrs followed by extraction with ethyl acetate. The ethyl acetate extract was washed with water until the pH was neutral, concentrated, dried under vacuum and analysed by High performance liquid chromatography (HPLC). Three peaks were detected at 368 nm (FIG. 5) and these corresponded to quercetin, kaempferol and isorhamnetin as confirmed by co-injection with reference standards. Kaempferol was isolated by column chromatography and its proton NMR (nuclear magnetic resonance) data matched with that reported in literature.

TABLE 3

[1] H and [13] C NMR data of Kaempferol isolated from the acid hydrolysis product. H denotes Hydrogen, C denotes carbon.

| $^1H$ | $^{13}C$ | $^{13}C$ |
|---|---|---|
| 6.10 (1H, d, H-6) | 145.96, C-2 | 93.82, C-8 |
| 6.32 (1H, d, H-8) | 135.59, C-3 | 160.51, C-9 |
| 6.91 (2H, d, H-3',5') | 175.51, C-4 | 101.77, C-10 |
| 8.03 (2H, d, H-2',6') | 156.43, C-5 | 121.73, C-1' |
| | 99.06, C-6 | 129.17, C-2', 6' |
| | 167.30, C-7 | 115.43, C-3', 5' |
| | | 159.23, C-4' |

HPLC conditions: —Column: Thermo Betasil, C18, 250× 4.6 mm, 5μ. Solvent system (isochratic): Methanol-Acetonitrile-Water (40:15:45 v/v/v) containing 1% acetic acid, flow rate 1 ml/min, detection at 368 nm. (Y-L Li et al, Molecules, 13, 1931-4 (2008); X. Liu et al, Food Chem. 109, 909-915 (2008).)

Sugar Analysis

After separation of flavonoids from the acid hydrolysis experiment, the aqueous layer after neutralization was tested for sugars present in the extract of *Costus pictus* using High performance thin layer chromatography (HPTLC) using reference sugars glucose, ribose, D galactose, fructose and rhamnose. Glucose, galactose and rhamnose were identified in the aqueous layer of acid hydrolysed *Costus pictus* extract, thereby indicating the presence of conjugates of these sugars in the extract (HPTLC FIG. 6a &6b).

HPTLC finger print of aqueous layer obtained from the acid hydrolysis experiment of *Costus pictus* D. Don was shown in FIGS. 6a and 6b. FIG. 6a provides HPTLC finger print of aqueous layer obtained from the acid hydrolysis experiment of *Costus pictus* D. Don extract in visible light and FIG. 6b provides HPTLC finger print of aqueous layer obtained from the acid hydrolysis experiment of *Costus pictus* D. Don extract in UV light.

HPTLC finger print (FIG. 6a and FIG. 6b) of aqueous layer of *Costus pictus* extract after acid hydrolysis shows the presence of sugars like glucose, galactose and rhamnose (Track 4) against reference standards glucose (Track 1), ribose (Track 2), D-galactose (Track 3), D-fructose (Track 4) and D-rhamnose (Track 7).

EXAMPLE 6

Liquid Chromatography-Mass Spectrometry (LCMS) Analysis

The extract was subjected to LCMS analysis on a Waters Quattro II triple quadrupole mass spectrometer having Waters Alliance HPLC system connected to it. The column used was Thermo-ODS-2 (250×4.6 mm, 5μ). A gradient elution using solvents 5% ACN (acetonitrile) in water (solvent A) and 95% ACN (acetonitrile) in water having 5 mM ammonium acetate (pH 4) was used. The composition of B was changed from 5% to 50 in 35 min, then to 80% in 45 min and maintained at 80% till 55 min and then maintained at 5% from 56 to 60 min. A photodiode array detector (PDA) detector (200-650 nm) was used to collect the high performance liquid chromatography (HPLC) data. The mass spectra were scanned in the range of 100-1000 Da (dalton) in 2 s. The Electrospray Ionisation (ESI) capillary was set to 3.5 kV (kilo volt) and the cone voltage was 40 V. Dry nitrogen was used as the nebulizer (10 liter per hour) and drying gas (250 liter per hour). The source temperature was 80° C.

As photodiode array detector (PDA) detector was available the UV data could be examined at different wavelengths. The chromatograms at 324 nm and 370 nm are given in FIGS. 7 & 8 respectively. The major constituents appear to be hydroxycinnamic acid derivatives (at 324 nm) and flavonoid glycosides (at 370 nm).

Summary of the Tables and Figures

Hydroxycinnamic Acid Derivatives

The Liquid chromatography-mass spectrometry (LCMS) chromatogram at 324 nm given in FIG. 9 clearly shows a number of components, mainly hydroxycinnamic acid derivatives.

These could be tentatively identified from the MS data given in Table 4. It is clear that the coumaric acid is part of many of these constituents. There are at least seven components of the chlorogenic acid family. These are coumaroyl quinic acids (CQA), an example of which is given below.

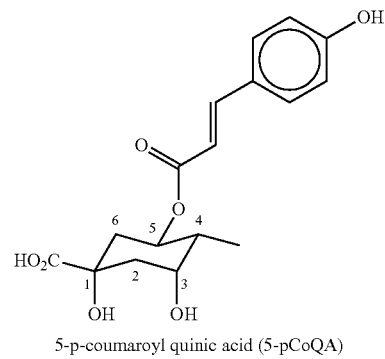

5-p-coumaroyl quinic acid (5-pCoQA)

TABLE 4

Identification of components of hydroxycinnamic acid from the mass spectral data.

| S. No | RT | M. Wt | MS Data (m/z) | Remarks |
|---|---|---|---|---|
| 1 | 5.48 | 342 | 360, 342, 325, 163, 145, 127 | Caffeoyl hexose/Disaccharide |
| 2 | 5.48 | 324 | 342, 325, 307, 289, 271, 163, 145 | Dehydrosugar/Disaccharide |
| 3 | 7.68 | 288 | 327, 311, 306, 271, 253 | Trihydroxyphenyl hexose |
| 4 | 9.58 | 356 | 374, 357, 139, 147 | Coumaric acid conjugate of hexaric acid |
| 5 | 10.60 | 356 | 374, 357, 227, 177, 147 | Coumaric acid conjugate of hexaric acid |
| 6 | 11.17 | 338 | 356, 339, 207, 147 | Coumaroyl quinic acid |
| 7 | 13.21 | 338 | 356, 339, 147 | " |
| 8 | 13.58 | 370 | 388, 371, 225, 207 | Sinapoyl rhamnose/dimer of sinapic acid & cinnamic acid |
| 9 | 15.42 | 386 | 404, 387, 225, 207 | Sinapoyl rhamnose/dimer of sinapic acid & coumaric acid |
| 10 | 15.90 | 338 | 356, 339, 207, 147 | Coumaroyl quinic acid |
| 11 | 16.98 | 338 | 356, 339, 147 | " |
| 12 | 18.48 | 338 | 356, 339, 147 | " |
| 13 | 19.04 | 338 | 356, 339, 147 | " |
| 14 | 19.89 | 338 | 356, 339, 147 | " |

RT—Retention time
M. Wt—Molecular weight
MS data—Mass spectrum data

Flavonoid Derivatives

Flavonoids are characterized by strong absorption at around 260 and 340-370 nm. Hence Photodiode array detector (PDA) data at 370 nm should be specific for flavonoids. The data shown in FIG. 10 indicate the presence of several flavonoid derivatives. At least 16 components could be detected and tentatively identified (Table 5). The fragment ions resulting from elimination of the sugar units clearly indicate the sequence of the sugar units in these glycosides. For example, the component having parent ion at m/z 757 correspond to quercetin triglycoside having a hexose and two rhamnose units. The sugar sequence could be similarly identified for all the other flavonoid glycoside components as shown in Table 5. All of them showed UV absorption maxima at around 260 and 350 nm confirming flavonoid glycosides. The chemical formulae of some of the flavonoid glycosides were obtained from accurate mass measurements of the parent ions (Table 6).

Acid hydrolysis of the extract gave quercetin, kaempferol and isorhamnetin as the aglycones. Their identities were confirmed by co-injection with standard reference compounds on HPLC. The presence of galactose, glucose and rhamnose has also been confirmed by sugar analysis following acid hydrolysis.

TABLE 5

Identification of components of flavonoids from mass spectral data. 16 components are detected and identified as flavonoid glycosides and free form.

| S. No | RT | M. Wt | MS Data(m/z) | $\lambda_{max}$ (wavelength) | Remarks |
| --- | --- | --- | --- | --- | --- |
| 1 | 15.73 | 756 | 757, 611, 465, 303 | 256, 352 | Quer-Hex-Rha-Rha |
| 2 | 17.13 | 740 | 741, 595, 449, 287 | 265, 338 | Kaem-Hex-Rha-Rha |
| 3 | 17.25 | 770 | 771, 625, 449, 317 | 266, 338 | IsoR-Hex-Rha-Rha |
| 4 | 17.34 | 610 | 611, 465, 303 | 260, 351 | Quer-Hex-Rha |
| 5 | 17.61 | 770 | 771, 625, 479, 317 | 260, 346 | IsoR-Hex-Rha-Rha |
| 6 | 18.14 | 610 | 611, 465, 303 | 260, 346 | Quer-Hex-Rha |
| 7 | 18.95 | 594 | 595, 449, 287 | 265, 347 | Kaem-Hex-Rha |
| 8 | 19.17 | 624 | 625, 479, 317 | 260, 347 | IsoR-hex-Rha |
| 9 | 19.32 | 464 | 465, 303 | 260, 352 | Quer-Hex |
| 10 | 20.07 | 594 | 595, 449, 287 | 265, 342 | Kaem-Hex-Rha |
| 11 | 20.35 | 624 | 625, 479, 317 | 260, 352 | IsoR-Hex-Rha |
| 12 | 21.34 | 448 | 449, 287 | 265, 346 | Kaem-Hex |
| 13 | 21.65 | 478 | 479, 317 | 265, 346 | IsoR-Hex |
| 14 | 28.75 | 302 | 303 | 265, 363 | Quercetin |
| 15 | 33.37 | 286 | 287 | 265, 363 | Kaempferol |
| 16 | 34.00 | 316 | 317 | 265, 363 | Isorhamnetin |

RT-Retention time, M.Wt-molecular weight, MS data-mass spectra data Quer-Quercetine, IsoR-Isorhamnetin, Kaem-Kaempferol, Hex-Hexose, Rha-Rhamnose

TABLE 6

The chemical formulae of some of the flavonoid glycosides obtained from accurate mass measurements of the parent ions.

| | Nominal mass | Exact mass (calculated) | Exact mass (measured) | Error (ppm) | Formula |
| --- | --- | --- | --- | --- | --- |
| 1 | 755 | 755.2035 | 755.2028 | -0.9 | $C_{33}H_{39}O_{20}$ |
| 2 | 739 | 739.2086 | 739.2080 | -0.8 | $C_{33}H_{39}O_{19}$ |
| 3 | 593 | 593.1506 | 593.1505 | -0.2 | $C_{27}H_{29}O_{15}$ |
| 4 | 463 | 463.0877 | 463.0873 | -0.9 | $C_{21}H_{19}O_{12}$ |
| 5 | 623 | 623.1612 | 623.1612 | 0 | $C_{28}H_{31}O_{16}$ |

The flavonoids appear to be mainly tri-, di- and monoglycosides of quercetin, kaempferol and isorhamnetin along with small amounts of the free flavonols. All tri- and diglycosides contain glucose/galactose/rhamnose whereas the monoglycosides contain only glucose or galactose.

EXAMPLE 7

Evaluation of effect of different fractions of fresh leaves of *Costus pictus* D. Don on streptozotocin-induced Type 1 diabetic model in Wistar rats.

The study was conducted in adult male Wistar rats weighing 200-250 gm for a period of 40 days (30 days of treatment and 10 days of induction). The animals were randomly divided into seven groups comprising six each. Diabetes was induced in all the groups except the normal control group by the intra peritoneal administration of streptozotocin at 50 mg/kg. After the induction of diabetes, one group was kept as diabetic untreated control and a positive control was maintained in which the animals were treated with standard drug, glibenclamide at 3 mg/kg orally. All the other diabetic induced groups were treated with different extracts at 300 mg/kg orally. The effect of the different fractions was assessed by measuring the fasting blood glucose level, post prandial blood glucose level, serum insulin levels and glycosylated Hb. The anti hyperlipidemic effect was assessed by the estimation of total cholesterol, triglyceride, LDL cholesterol, HDL cholesterol, VLDL, muscle glycogen and liver glycogen. The antioxidant effects of the different extracts were assessed by the measuring TBARS, superoxide dismutase (SOD), catalase, reduced glutathione (GSH) and glutathione peroxidase levels (GPx). TBARS was determined by TBA assay (Ohkawa et al., 1979), SOD was measured using the nitroblue tetrazolium reduction method (Kakkar et al., 1984), Catalase was assayed using the method described by Aebi (1974). GPx was measured as described by Flohe and Gunzler (1984), GSH was measured as per the method of Jollow et al., (1974). Histopathological examination of pancreas was conducted to assess the antidiabetic effect of the different fractions of *Costus pictus* D. Don.

The experimental design was as follows:

Group 1—Normal control.

Group 2—Diabetic control—untreated diabetic animals.

Group 3—Positive control—diabetic animals treated with glibenclamide at 3 mg/kg orally.

Group 4—diabetic animals treated with methanolic extract of fresh leaves of *Costus pictus* D. Don, the extract has low oxalic acid and/or oxalates content (Sample 2 prepared as per Example 1) at 40 mg/kg orally.

Group 5—diabetic animals treated silica purified ethyl acetate extract of 90% methanolic extract of fresh leaves of *Costus pictus* D. Don (Sample 5 prepared as per Example 4) and the extract has low oxalic acid and/or oxalates content at 40 mg/kg orally.

Group 6—diabetic animals treated with ethyl acetate extract of 90% methanol extract of fresh leaves of *Costus pictus* D. Don (Sample 4 prepared as per Example 3) and the extract has low oxalic acid and/or oxalates content at 40 mg/kg orally.

Group 7—diabetic animals treated with methanolic extract of fresh leaves of *Costus pictus* D. Don. (Sample 1 prepared as per Example 1) at 40 mg/kg orally.

Results:

Blood Glucose Level

The results of the study are presented in Table 1. The different fraction of *Costus pictus* D. Don showed a reduction in the blood glucose level on day 15 and day 30. The reduction in blood glucose level showed by group 5 having low oxalic acid and/or oxalates content was more than the other treated groups. 90% methanol extract of *Costus pictus* D. Don with oxalic acid showed 3.45 times reduction in blood glucose level. 90% methanol extract of *Costus pictus*

D. Don having low oxalic acid and/or oxalates content showed 4.55 times reduction in blood glucose level in streptozotocin-induced diabetes.

TABLE 1

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) and methanolic extract with oxalic acid (Group 7) on blood glucose levels (mg/dl) in streptozotocin-induced diabetes.

| Groups | $0^{th}$ day | $15^{th}$ day | $30^{th}$ day |
|---|---|---|---|
| Group 1 | 70 | 71 | 71 |
| Group 2 | 320 | 315 | 420 |
| Group 3 | 321 | 126 | 71 |
| Group 4 | 325 | 185 | 71.5 |
| Group 5 | 322 | 175 | 70.1 |
| Group 6 | 323 | 178 | 70.6 |
| Group 7 | 320 | 183 | 92.5 |

Oral Glucose tolerance test (OGTT) was performed following a glucose challenge of 2.5 g/kg by oral gavage. Blood glucose was recorded at 30 min ($PPG_1$), 60 min ($PPG_2$), 120 min ($PPG_3$) and 240 min ($PPG_4$), after the glucose challenge on day 1, day 15 and day 30 of the study.

The results of the study are presented in Table 2. The different fraction of *Costus pictus* D. Don showed a reduction in the PPG level after 240 min. The reduction in PPG showed by group 5 having low oxalic acid and/or oxalates content was more than the other treated groups.

TABLE 2

Effect of methanolic extract having low oxalic acid and/or oxalates content (group 4), ethyl notate extract of 90% methanol extract having low oxalic acid and/or oxalates content (group 6) and its silica purified part having low oxalic acid and/or oxalates content (group 5) and methanolic extract with oxalic acid (group 7) on post-prandial glucose levels.

| Groups | PPG1. 1 | PPG1. 15 | PPG1. 30 | PPG2. 1 | PPG2. 15 | PPG2. 30 |
|---|---|---|---|---|---|---|
| Group 1 | 268.2 | 182.4 | 228.4 | 128.6 | 132.1 | 149.6 |
| Group 2 | 511.6 | 330.8 | 395.4 | 499.3 | 345.8 | 402.1 |
| Group 3 | 522.8 | 318.3 | 232.1 | 478.4 | 217.4 | 240.4 |
| Group 4 | 318.4 | 219.9 | 227.8 | 184.8 | 134.2 | 230.8 |
| Group 5 | 320.5 | 201.4 | 217.4 | 240.8 | 102.4 | 262.4 |
| Group 6 | 328.4 | 208.4 | 232.5 | 252.1 | 110.4 | 298.1 |
| Group 7 | 325.3 | 224.8 | 292.1 | 272.4 | 128.9 | 288.1 |

| Groups | PPG3. 1 | PPG3. 15 | PPG3. 30 | PPG4. 1 | PPG4. 15 | PPG4. 30 |
|---|---|---|---|---|---|---|
| Group 1 | 92.8 | 95.6 | 110.7 | 73.4 | 71.8 | 75.8 |
| Group 2 | 378.8 | 282.8 | 323.8 | 332.1 | 235.9 | 281.4 |
| Group 3 | 332.1 | 115.3 | 177.3 | 201.9 | 104.8 | 69.8 |
| Group 4 | 141.3 | 98.6 | 90.2 | 102.1 | 70.8 | 73.6 |
| Group 5 | 134.3 | 93.6 | 91.8 | 99.7 | 70.6 | 72.8 |
| Group 6 | 148.2 | 96.4 | 92.4 | 101.4 | 71.2 | 73.4 |
| Group 7 | 201.4 | 104.8 | 106.4 | 110.5 | 90.8 | 95.2 |

Lipid Profile and Tissue Glycogen Levels

The results of the study on the effect of lipid profile and tissue glycogen levels are presented in Table. 3 and Table. 4 respectively. The results of total cholesterol, triglycerides, LDL and VLDL showed a reduction when compared to the diabetic untreated control. High Density Lipoproteins values increased in the sample treated groups when compared to diabetic untreated control. An increase in the muscle and liver glycogen levels were observed in the sample treated groups when compared to diabetic untreated group. The effect of different fraction on lipid profile and tissue glycogen levels was more in group 5.

TABLE 3

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) and ethanolic extract with oxalic acid (group 7) on total cholesterol, triglyceride, LDL cholesterol, HDL cholesterol, VLDL levels.

| Groups | TC (mg/dl) | TG (mg/dl) | LDL (mg/dl) | HDL (mg/dl) | VLDL (mg/dl) |
|---|---|---|---|---|---|
| Group1 | 121 | 98 | 49 | 52 | 20 |
| Group 2 | 241 | 196 | 181 | 20 | 40 |
| Group 3 | 128 | 100 | 56 | 52 | 20 |
| Group 4 | 130 | 103 | 51 | 58 | 21 |
| Group 5 | 128 | 95 | 49 | 60 | 19 |
| Group 6 | 129 | 100 | 50 | 59 | 20 |
| Group 7 | 140 | 110 | 59 | 48 | 28 |

TABLE 4

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) and methanolic extract with oxalic acid (group 7) on muscle glycogen and liver glycogen levels.

| Groups | Muscle glycogen (mg/g tissue) | Liver glycogen (mg/g tissue) |
|---|---|---|
| Group1 | 10 | 48 |
| Group 2 | 2 | 20 |
| Group 3 | 8 | 46 |
| Group 4 | 9.0 | 44 |
| Group 5 | 9.3 | 47 |
| Group 6 | 9.2 | 47 |
| Group 7 | 8.3 | 41 |

Insulin and Glycosylated Hb Levels

The effect of the different extracts on insulin and glycosylated Hb levels is presented on Table 5. Sample treated groups showed an increase in the insulin level and a decrease in the glycosylated hameoglobin level when compared to diabetic untreated group. The effect was more in group 5.

TABLE 5

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) and methanolic extract with oxalic acid (group 7) on insulin and glycosylated Hb levels.

| Groups | Insulin level (µU/ml) | Glycosylated Hb (% total Hb) |
|---|---|---|
| Group 1 | 16 | 0.5 |
| Group 2 | 7 | 0.9 |
| Group 3 | 13 | 0.5 |
| Group 4 | 15 | 0.5 |
| Group 5 | 15.4 | 0.5 |
| Group 6 | 15.2 | 0.5 |
| Group 7 | 14.1 | 0.6 |

Antioxidant Enzymes

The effect of the extracts on antioxidant enzyme levels is presented in Table. 6. The antioxidant enzyme levels of SOD, catalase. GSH and GPx were increased in the sample treated groups and a reduction in the TBARS level was observed in all the sample treated groups when compared to the diabetic untreated group. The effect on the antioxidant enzymes and TBARS were more in group 5.

TABLE 6

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) and methanolic extract with oxalic acid (group 7) on antioxidant enzyme levels.

| Groups | TBARS (mM MDA/ 100 g) | SOD (U/mg protein) | Catalase (nM $H_2O_2$ decomposed/ s/g | GSH (mg/ 100 g) | GPx (U/mg of protein) |
|---|---|---|---|---|---|
| Group 1 | 0.66 | 5.04 | 66.45 | 49.68 | 11.23 |
| Group 2 | 2.01 | 2.16 | 40.12 | 22.45 | 3.96 |
| Group 3 | 0.80 | 2.96 | 59.36 | 38.12 | 7.54 |
| Group 4 | 0.91 | 4.21 | 63.25 | 45.12 | 9.35 |
| Group 5 | 0.95 | 4.60 | 64.12 | 48.32 | 9.78 |
| Group 6 | 0.93 | 4.40 | 63.89 | 47.88 | 9.60 |
| Group 7 | 0.85 | 3.99 | 61.57 | 43.87 | 8.48 |

Pancreatic Histopathology

Histopathological examination of the pancreas of normal group revealed normal architecture. Administration of streptozotocin decreased the number of β cells and the untreated diabetic group revealed shrunken islets with degenerative necrosis. In the sections of group 3, group 4, group 5, group 6 and group 7 islets appeared less shrunken than the untreated diabetic control group and increased number of β cells was also observed. There were also a reduction in the number of initiated lymphocytes and macrophages. The histopathological observations were predominant in group 5. The mean number of islets in group 1 was 36. In group 2, the mean number of islets was 5 while in group 3 it was 18.66. The mean number of islets in sample treated groups ie, Groups 4, 5, 6 & 7 were 18, 22.83, 19.66 and 17.11 respectively. This shows that there was regeneration of the damaged islet cells in the treated groups, the maximum of which was seen in group 5. Moreover, on immune histochemistry groups 4 (FIG. 14), 5 (FIG. 15), 6 (FIG. 16) and 7 (FIG. 17) showed intensely stained beta cells and an increase in the number of beta cells in the islets compared to both diabetic control as well as the normal control. The beta cells in groups 2 were extremely sparse. The beta cells in group 3 were moderately stained and comparable to group 1.

EXAMPLE 8

Evaluation of effect of different fractions of *Costus pictus* D. Don on high fat diet-induced insulin resistance model with C57/BL6J mice.

The study was designed to evaluate the effect of different fractions of *Costus pictus* D. Don on high fat-induced resistance Type 2 diabetic model (HFD). Six week-old C57Bl/6J mice were allowed free access to food and water. They were housed under identical standard conditions. The animals were kept for acclimatization for a period of 7 days. After 7 days, the mice were randomly divided into six groups of six mice each. The normal control group was treated with normal regular diet and the rest of the animals were fed with high fat diet for 6 weeks. After 6 weeks, methanolic extract of fresh leaves of *Costus pictus* D. Don, and the extract had low oxalic acid and/or oxalates content, silica purified ethyl acetate extract of methanolic extract of fresh leaves of *Costus pictus* D. Don where the extract had low oxalic acid and/or oxalates content and ethyl acetate extract of 90% methanolic extract of fresh leaves of *Costus pictus* D. Don where the extract had low oxalic acid and/or oxalates content were administered at 40 mg/kg p.o. for 6 consecutive weeks. The experimental design was as follows:

Group 1—Normal control treated with normal regular diet.

Group 2—HFD treated group for 6 weeks.

Group 3—HFD for 6 weeks and Standard drug treated group for 6 weeks-metformin.

Group 4—HFD for 6 weeks and methanolic extract of fresh leaves of *Costus pictus* D. Don where the extract had low oxalic acid and/or oxalates content (Sample 2 prepared as per example 1) at 40 mg/kg orally for 6 weeks.

Group 5—HFD for 6 weeks and silica purified ethyl acetate extract of 90% methanolic extract of fresh leaves of *Costus pictus* D. Don where the extract had low oxalic acid and/or oxalates content (Sample 5 prepared as per example 4) at 40 mg/kg orally for 6 weeks.

Group 6—HFD for 6 weeks and ethyl acetate extract of 90% methanol extract of fresh leaves of *Costus pictus* D. Don where the extract had low oxalic acid and/or oxalates content (Sample 4 prepared as per example 3) at 40 mg/kg orally for 6 weeks.

Observations

Body weights were determined biweekly. At the end of experimental period, blood samples were collected to determine plasma glucose, insulin, leptin, glycosylated hemoglobin, triglycerides, total cholesterol, LDL, HDL and VLDL.

Body Weight

The results of the body weight of the animals are displayed in Table. 1. At the end of 6 weeks, the mean body weight of all the animals increased from 15 g to nearly 60 g. After the end of 12 weeks, the sample treated groups showed a reduction in the body weight. The effect was almost similar in all the treated groups except metformin treated group. Among the sample treated groups (group 4, 5 & 6), group 5 showed similar effect to the standard drug (metformin) treated group.

TABLE 1

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) on body weight.

| Groups | Body weight at biweekly interval (in grams) | | | | | | |
|---|---|---|---|---|---|---|---|
| | 0 | 2 | 4 | 6 | 8 | 10 | 12 |
| Gr. 1 | 15 | 18 | 22 | 25 | 28 | 32 | 35 |
| Gr. 2 | 15 | 30 | 45 | 60 | 60 | 58 | 56 |
| Gr. 3 | 15 | 30 | 46 | 61 | 48 | 35 | 35 |
| Gr. 4 | 13 | 28 | 44 | 62 | 52 | 40 | 39 |
| Gr. 5 | 15 | 30 | 46 | 62 | 48 | 38 | 35 |
| Gr. 6 | 15 | 30 | 46 | 61 | 50 | 39 | 37 |

Blood Glucose

The results of the blood glucose level are depicted in Table. 2. The results showed a reduction in the blood glucose level of all the sample treated groups (group 4, 5 & 6). The reduction in blood glucose activity was high in group 5.

TABLE 2

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) on blood glucose level.

| Groups | Blood glucose (mg/dl) |
| --- | --- |
| Gr. 1. | 80 |
| Gr. 2. | 229 |
| Gr. 3. | 100 |
| Gr. 4. | 145 |
| Gr. 5. | 140 |
| Gr. 6. | 141 |

Lipid Profile:

The results of the total cholesterol, triglycerides, LDL, HDL and VLDL are given in Table 3. The TC level of HFD treated group was high. All the sample treated groups showed a reduction in TC level. Similarly TG, LDL and VLDL showed higher values in HFD treated group. The LDL values of HFD treated group were low. But all the sample treated groups showed a reduction in the TG, LDL, VLDL and an increase in HDL. Among the sample treated groups (group 4, 5 & 6), group 5 showed a reduction in the lipid profile which was almost similar to the standard drug (metformin) treated group.

TABLE 3

Effect of methanolic extract having low oxalic acid and/or oxalates content (group 4), ethyl acetate extract of 90% methanol extract having low, oxalic acid and/or oxalates content (group 6) and its silica purified part having low oxalic acid and/or oxalates content (group 5) on lipid profile in high fat diet induced diabetes mellitus.

| Groups | TC (mg/dl) | TG (mg/dl) | LDL (mg/dl) | HDL (mg/dl) | VLDL (mg/dl) |
| --- | --- | --- | --- | --- | --- |
| Gr. 1. | 120 | 30 | 24 | 90 | 6 |
| Gr. 2. | 180 | 65 | 102 | 65 | 13 |
| Gr. 3. | 122 | 30 | 17 | 99 | 6 |
| Gr. 4. | 124 | 20 | 26 | 94 | 4 |
| Gr. 5. | 120 | 30 | 17 | 97 | 6 |
| Gr. 6. | 122 | 25 | 21 | 96 | 5 |

Serum Insulin Levels

The results of serum insulin and glycosylated hemoglobin are shown in Table. 4. The HFD treated group showed an increase in insulin values. On the other hand, the sample treated groups (group 4, 5 & 6) showed a reduction in the serum insulin and glycosylated hemoglobin values. Among the samples treated group, the effect is more in group 5 which showed a more similar activity to the standard drug treated group.

TABLE 4

Effect of methanolic extract having low oxalic acid and/or oxalates content (group 4), ethyl acetate extract of 90% methanol extract having low oxalic acid and/or oxalates content (group 6) and its silica purified part having low oxalic acid and/or oxalates content (group 5) on serum insulin, leptin and glycosylated hemoglobin levels in high fat diet induced diabetes mellitus.

| Groups | Insulin (ng/ml) | Glycosylated Hb (% of total Hb) |
| --- | --- | --- |
| Gr. 1. | 0.7 | 0.5 |
| Gr. 2. | 3.8 | 1.0 |
| Gr. 3. | 1.7 | 0.5 |
| Gr. 4. | 2.2 | 0.6 |
| Gr. 5. | 1.7 | 0.5 |
| Gr. 6. | 2.0 | 0.5 |

EXAMPLE 9

In vitro insulin secretogogue effect of the different fractions of *Costus pictus* D. Don using isolated mouse islets.

Procedure

I. Animals

Four to six weeks old male mice (Swiss albino strain; weighing 25±2 g) used for the study were maintained in the optimum environmental conditions.

II. Isolation of Islets

Pancreata isolated from animals which were euthanized with $CO_2$ anesthesia according the method of Shewadae et al., (1999) was removed aseptically. Washed thrice with Hank's Balanced Salt Solution (HBSS) and were subjected to collagenase digestion at 37° C. The pancreata was incubated in the dissociation medium (Dulbecco's modified minimum essential medium (DMEM) supplemented with collagenase, Soybean Trypsin Inhibitor and Bovine Serum Albumin fraction V) for 10 minutes. The procedure was repeated thrice and the dissociation was stopped by addition of chilled DMEM with 10% fetal bovine serum to the pancreatic digest. The mixture was centrifuged at 200×g for 10 minutes and the supernatant was discarded. After two washings with DMEM, the pellet was seeded in culture flasks containing DMEM pH-7.2 supplemented with 10% fetal bovine serum. The flasks were incubated at 37° C. in a $CO_2$ incubator.

III. Assessment of Islet Viability and Specificity

The viability of the islets was checked by Trypan blue dye exclusion test (Warburton and James, 1995) and this estimate had shown >98% of the cells were viable.

IV. Preparation of the Extracts and Standards

The extracts and glibenclamide (10 nM) were dissolved in HBSS at required concentrations. The HBSS alone served as negative control and glibenclamide served as positive control. Three groups were given extract of *Costus pictus* D. Don having low oxalic acid and/or oxalates content as follows Group 1—90% methanolic extract of fresh leaves of *Costus pictus* D. Don where the extract had low oxalic acid and/or oxalates content (Sample 2 prepared as per example 1).

Group 2—silica purified ethyl acetate extract of 90% methanolic extract of fresh leaves of *Costus pictus* D. Don where the extract had low oxalic acid and/or oxalates content. (Sample 5 prepared as per example 4)

Group-3 ethyl acetate extract of 90% methanolic extract of fresh leaves of *Costus pictus* D. Don where the extract had low oxalic acid and/or oxalates content. (Sample 4 prepared as per example 3)

V. Assessment of Insulin Secretogogue Effect In Vitro

The islets were hand-picked under sterile conditions and islets were placed in one well of 24 well plate in DMEM containing 10% FBS. After 24 hours of recovery period, the spent medium was removed and the cells were washed with HBSS. The cells were given an initial incubation in 1 mL of HBSS for 30 minutes at 37° C. Then the islets were incubated with various concentrations of test material (25-200 µg/mL, at five doses) and positive control glibenclamide (10 nM). The islets were then incubated for at 37° C. for 30 minutes and 50 µL of supernatants were collected. All the samples were assayed for insulin content by ELISA method. The experiments were performed in triplicates.

Results

TABLE 5

In vitro insulin secretogogue effect of the extract E2 on isolated pancreatic islets

| Groups | Zero minutes Concentration of insulin (ng/mL) | Thirty minutes Concentration of insulin (ng/mL) |
| --- | --- | --- |
| Cells alone | 0.4 | 1.53 |
| Glibenclamide (10 nM) | 0.97 | 3.77 |
| Extract(25 µg/mL) Group 1 | 0.33 | 2.50 |
| Extract(25 µg/mL) - group 2 | 0.69 | 3.12 |
| Extract(25 µg/mL) - group 3 | 0.41 | 3.01 |
| Extract(50 µg/mL) - group 1 | 0.49 | 3.17 |
| Extract(50 µg/mL) - group 2 | 0.59 | 4.11 |
| Extract(50 µg/mL) - group 3 | 0.59 | 3.55 |

Inference

In the assessment of insulin secretogogue effect, at basal level there was no significant variations in the insulin levels. At 25 µg/mL extract concentration there was an increase in the level of insulin released in the medium. At 50 µg/mL concentration, the release was highly significant and comparable with that of positive control (glibenclamide). The increase in the insulin concentration was higher in group 2.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of treating diabetes comprising administering an effective amount of a composition to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

2. A method of decreasing blood glucose level comprising administering an effective amount of a composition to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

3. A method of decreasing HbA1c level comprising administering an effective amount of a composition to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

4. A method of increasing serum insulin level comprising administering an effective amount of a composition of to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

5. A method of increasing liver and muscle glycogen comprising administering an effective amount of a composition to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

6. A method of increasing insulin secretogogue effect comprising administering an effective amount of a composition to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

7. A method for regeneration of pancreatic beta cells comprising administering an effective amount of a composition to a subject in need thereof, the composition comprising:
   an extract of *Costus pictus* D. Don, the extract comprising hydroxycinnamic acid derivatives and flavonols, and, wherein a total of oxalic acid and oxalates content in the extract is less than about 15%.

8. The method of treating diabetes of claim 1, wherein the extract of *Costus pictus* D. Don of claim 1 is prepared by:
   a) cleaning a starting material of *Costus pictus* D. Don;
   b) cutting the product of step (a);
   c) extracting the product of step (b) with 90% methanol;
   d) refluxing the product of step (c) for at the boiling temperature (60-70° C.) of methanol to obtain a residue and a supernatant;
   e) filtering to separate the residue and the supernatant of step (d);
   f) concentrating the supernatant of step (e) to obtain a concentrated methanol extract;
   g) drying the concentrated methanol extract of step (f) to obtain a powder of the methanol extract;
   h) mixing the powder of step (g) with water;
   i) heating the product of step (h) to obtain a residue and a supernatant;
   j) separating the residue from the supernatant;
   k) drying the residue of step j) to obtain a dry powder comprising about 10% of oxalic acid, whereby the dry powder is the extract of *Costus pictus* D. Don of claim 1.

* * * * *